(12) United States Patent
Wu et al.

(10) Patent No.: US 11,584,750 B2
(45) Date of Patent: Feb. 21, 2023

(54) CRYSTALLINE FORMS OF (S)-4-AMINO-6-((1-(3-CHLORO-6-PHENYLIMIDAZO[1,2-B]PYRIDAZINE-7-YL)ETHYL)AMINO)PYRIMIDINE-5-CARBONITRILE AS INHIBITORS OF PHOSPHATIDYLINOSITOL-3-KINASE

(71) Applicant: HUTCHISON MEDIPHARMA LIMITED, Shanghai (CN)

(72) Inventors: Zhenping Wu, Shanghai (CN); Wenji Li, Shanghai (CN); Ling Feng, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 121 days.

(21) Appl. No.: 17/049,122

(22) PCT Filed: Apr. 18, 2019

(86) PCT No.: PCT/CN2019/083216
§ 371 (c)(1),
(2) Date: Oct. 20, 2020

(87) PCT Pub. No.: WO2019/201298
PCT Pub. Date: Oct. 24, 2019

(65) Prior Publication Data
US 2021/0238180 A1    Aug. 5, 2021

(30) Foreign Application Priority Data
Apr. 20, 2018 (CN) .......................... 201810360892.4

(51) Int. Cl.
*A61K 31/5025* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .......................... A61K 31/5025; C07D 487/04
USPC ......................................... 514/248; 544/236
See application file for complete search history.

(56) References Cited

U.S. PATENT DOCUMENTS 10,208,066 B2    2/2019    Wei-Guo et al.

FOREIGN PATENT DOCUMENTS

| WO | WO 2016/045591 | 3/2016 |
| WO | WO 2016/045591 A1 | 3/2016 |
| WO | WO-2019201298 A1 * | 10/2019 ........... A61K 31/506 |

OTHER PUBLICATIONS

Jordan, V. C. Nature Reviews: Drug Discovery, 2, 2003, 205.*
Hackam, et al. JAMA, 296(14), 2006, 1731-1732.*
Written Opinion of the International Searching Authority for International Application No. PCT/CN2019/083216 dated Jul. 24, 2019, 5 pages.
Brittain, H. G., "Polymorphism in Pharmaceutical Solids", *Drugs and Pharmaceutical Sciences*, Informa Healthcare, vol. 192, (2009).
Caira, M. R., "crystalline polymorphism of organic compounds", *Topics in Current Chemistry*, 198, pp. 163-208, (1998).
Fujiwara et al., "First-principles and direct design approaches for the control of pharmaceutical crystallization", *Journal of Process Control*, 15(5), pp. 493-504, (2005).
"Guidance for Industry on ANDAs: Pharmaceutical Solid Polymorphism; Chemistry, Manufacturing, and Controls Information; Availability", *Federal Register*, 72, pp. 37244-37245, (2007).
Morissette et al., "High-throughput crystallization: polymorphs, salts. co-crystals and solvates of pharmaceutical solids", *Advanced Drug Delivery Reviews*, 56(3), pp. 275-300, (2004).
Variankaval et al., "From form to function: Crystallization of active pharmaceutical ingredients", *AIChE Journal*, 54(7), pp. 1682-1688, (2008).

* cited by examiner

*Primary Examiner* — Douglas M Willis
(74) *Attorney, Agent, or Firm* — Hoxie & Associates LLC

(57) ABSTRACT

The present invention belongs to the pharmaceutical field, and provides crystalline forms, solvates and the crystalline forms thereof of the compound (S)-4-amino-6-((1-(3-chloro-6-phenylimidazo[1,2-b]pyridazin-7-yl)ethyl)amino)pyrimidine-5-carbonitrile of the formula shown below, and the pharmaceutical compositions comprising the same as well as the methods of preparing the same and the use thereof.

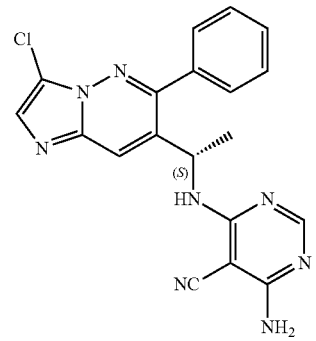

22 Claims, 9 Drawing Sheets

CRYSTALLINE FORMS OF (S)-4-AMINO-6-((1-(3-CHLORO-6-PHENYLIMIDAZO[1,2-B]PYRIDAZINE-7-YL)ETHYL)AMINO)PYRIMIDINE-5-CARBONITRILE AS INHIBITORS OF PHOSPHATIDYLINOSITOL-3-KINASE

CROSS REFERENCE TO RELATED APPLICATIONS

This application is a United States Application under 35 U.S.C. 371 claiming benefit of International Application No. PCT/CN2019/083216, filed on Apr. 18, 2019, which claims the benefit of Chinese Patent Application No. 201810360892.4 filed on Apr. 20, 2018, the contents of each of which are incorporated herein by reference.

FIELD OF THE INVENTION

The present invention belongs to the pharmaceutical field, and provides novel crystalline forms, solvates and the crystalline forms thereof of the compound (S)-4-amino-6-((1-(3-chloro-6-phenylimidazo[1,2-b]pyridazin-7-yl)ethyl)amino)pyrimidine-5-carbonitrile, and the pharmaceutical compositions comprising the same as well as the methods of preparing the same and the use thereof.

BACKGROUND OF THE INVENTION

PI$_3$K (phosphatidylinositol-3-kinase) is a family of lipid kinases, and abnormality in PI$_3$K-mediated signaling pathway is believed to play critical roles in the occurrence and development of a variety of malignant tumors. Dysregulation and overactivation of the PI$_3$K/AKT pathway has been found in cancer cells. PI$_3$Kδ is also involved in mammalian immune system functions, including signal transduction of B-cell, T-cell, mast cell, dendritic cell, neutrophil, NK cell, and monocyte/phagocyte. Studies have shown that, inhibition of PI$_3$K, including selective inhibition of PI$_3$Kδ activity is useful for the treatment of autoimmune diseases or inflammatory diseases, such as: systemic lupus erythematosus, rheumatoid arthritis, multiple sclerosis, allergic rhinitis, chronic obstructive pulmonary disease, psoriasis, and asthma. In addition, inhibition of PI$_3$K, including selective inhibition of PI$_3$Kδ activity is also useful in treating cancer, especially hematological malignancy such as: lymphoma, leukemia, and multiple myeloma.

The relevant compound (S)-4-amino-6-((1-(3-chloro-6-phenylimidazo[1,2-b]pyridazin-7-yl)ethyl)amino)pyrimidine-5-carbonitrile of the present invention, with the chemical structure of Formula A, has the effect of effectively inhibiting PI$_3$K, especially inhibiting PI$_3$Kδ activity. Thus, it is useful in treating diseases responsive to inhibition of PI$_3$K activity, such as the treatment of autoimmune diseases, inflammatory diseases, and cancer.

Formula A

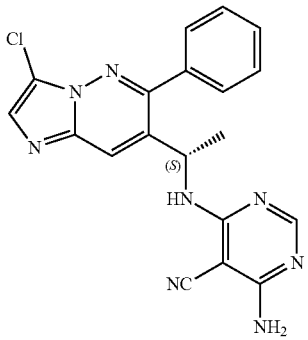

The phenomenon that a compound could exist in two or more crystal structures is known as polymorphism. Many compounds may exist as various polymorph crystals and also in a solid amorphous form. However, until polymorphism of a compound is discovered, it is highly unpredictable (1) whether a particular compound will exhibit polymorphism, (2) how to prepare any such unknown polymorphs, and (3) how are the properties, such as stability, of any such unknown polymorphs. See, e.g., J. Bernstein "Polymorphism in Molecular Crystals", Oxford University Press, (2002).

Since the properties of a solid material depend on the structure as well as on the nature of the compound itself, different solid forms of a compound can and often do exhibit different physical and chemical properties as well as different biopharmaceutical properties. Differences in chemical properties can be determined, analyzed and compared through a variety of analytical techniques. Those differences may ultimately be used to differentiate among different solid forms. Furthermore, differences in physical properties, such as solubility, and biopharmaceutical properties, such as bioavailability, are also of importance when describing the solid state of a pharmaceutical compound. Similarly, in the development of a pharmaceutical compound, such as compound of Formula A, new crystalline and amorphous forms of the pharmaceutical compound are also of importance.

The compound (S)-4-amino-6-((1-(3-chloro-6-phenylimidazo[1,2-b]pyridazin-7-yl)ethyl) amino)pyrimidine-5-carbonitrile as well as the preparation thereof was described in patent application WO2016045591A1.

CONTENTS OF THE INVENTION

Summary

Upon extensive explorations and researches, we have found that compound of Formula A (S)-4-amino-6-((1-(3-chloro-6-phenylimidazo[1,2-b]pyridazin-7-yl)ethyl)amino) pyrimidine carbonitrile can exist in different crystalline forms (i.e. polymorphs), and can form solvates with certain solvents. We have made extensive studies on the polymorphs of compound of Formula A and have finally prepared and determined the crystalline forms which meet the requirement of pharmaceutical use. Based on these studies, the present invention provides the various crystalline forms of compound of Formula A and the solvates and the crystalline forms thereof, which are designated as Form I, Form IV, Form V, Form VI, and Form VIII respectively.

In one aspect, the polymorphs of compound of Formula A or the solvates thereof provided by the present invention have good crystallinity and good stability and are non-hygroscopic.

Firstly, the present invention provides crystalline Form I of (S)-4-amino-6-((1-(3-chloro-6-phenylimidazo[1,2-b]pyridazin-7-yl)ethyl)amino)pyrimidine-5-carbonitrile, i.e. Form I of compound of Formula A.

Secondly, the present invention provides crystalline Form IV of (S)-4-amino-6-((1-(3-chloro-6-phenylimidazo[1,2-b]pyridazin-7-yl)ethyl)amino)pyrimidine-5-carbonitrile, i.e. Form IV of compound of Formula A.

Further, the present invention provides crystalline Form V of (S)-4-amino-6-((1-(3-chloro-6-phenylimidazo[1,2-b]pyridazin-7-yl)ethyl)amino)pyrimidine-5-carbonitrile, i.e. Form V of compound of Formula A.

Even further, the present invention provides the solvates of (S)-4-amino-6-((1-(3-chloro-6-phenylimidazo[1,2-b]

pyridazin-7-yl)ethyl)amino)pyrimidine-5-carbonitrile, which are acetone solvate, and water and i-propanol solvate of compound of Formula A.

Even further, the present invention provides the solvates of (S)-4-amino-6-((1-(3-chloro-6-phenylimidazo[1,2-b]pyridazin-7-yl)ethyl)amino)pyrimidine-5-carbonitrile, which are monoacetone solvate, and water and i-propanol solvate (containing 3 molecules of water and 0.5 molecule of i-propanol) of compound of Formula A.

Even further, the present invention provides monoacetone solvate of (S)-4-amino-6-((1-(3-chloro-6-phenylimidazo[1,2-b]pyridazin-7-yl)ethyl)amino)pyrimidine-5-carbonitrile, which is Form VI of compound of Formula A.

Even further, the present invention provides water and i-propanol solvate (containing 3 molecules of water and 0.5 molecule of i-propanol) of (S)-4-amino-6-((1-(3-chloro-6-phenylimidazo[1,2-b]pyridazin-7-yl)ethyl)amino)pyrimidine-5-carbonitrile, which is Form VIII of compound of Formula A.

In another aspect, the present invention provides the methods of preparation for the crystalline forms of compound of Formula A, the solvates of compound of Formula A and the crystalline forms thereof (such as Form I, Form IV, Form V, Form VI, and Form VIII), which are reproducible and easy in operation.

In still another aspect, the present invention provides the pharmaceutical compositions comprising an effective amount of one or more of the crystalline forms of compound of Formula A, the solvates of compound of Formula A and the crystalline forms thereof (such as Form I, Form IV, Form V, Form VI, and Form VIII), and remaining amount of at least one pharmaceutically acceptable carrier.

The present invention further provides a method of treating diseases responsive to inhibition of PI$_3$K activity, comprising administering to a subject in need thereof an effective amount of one or more of the crystalline forms of compound of Formula A, the solvates of compound of Formula A and the crystalline forms thereof (such as Form I, Form IV, Form V, Form VI, or Form VIII) of the present invention.

The present invention further provides a use of the crystalline forms of compound of Formula A, the solvates of compound of Formula A and the crystalline forms thereof (such as Form I, Form IV, Form V, Form VI, or Form VIII) in the manufacture of a medicament for treating diseases responsive to inhibition of PI$_3$K activity. In some embodiments, said diseases responsive to inhibition of PI$_3$K activity are selected from autoimmune diseases, inflammatory diseases, and cancer (preferably hematological malignancy). In some embodiments, said autoimmune diseases or inflammatory diseases are selected from systemic lupus erythematosus, rheumatoid arthritis, multiple sclerosis, allergic rhinitis, chronic obstructive pulmonary disease, psoriasis, and asthma. In some embodiments, said cancer is selected from lymphoma (such as Hodgkin's lymphoma, non-Hodgkin's lymphoma, mantle cell lymphoma, follicular lymphoma, small lymphocytic lymphoma, marginal zone lymphoma, Burkitt lymphoma, B cell lymphoma, T cell lymphoma, NK cell lymphoma, and diffuse large B-cell lymphoma), leukemia (such as chronic lymphocytic leukemia, acute lymphocytic leukemia, acute myeloid leukemia, and chronic myelogenous leukemia), multiple myeloma, and Waldenstrom's macroglobulinemia.

DEFINITIONS

Figure 1:
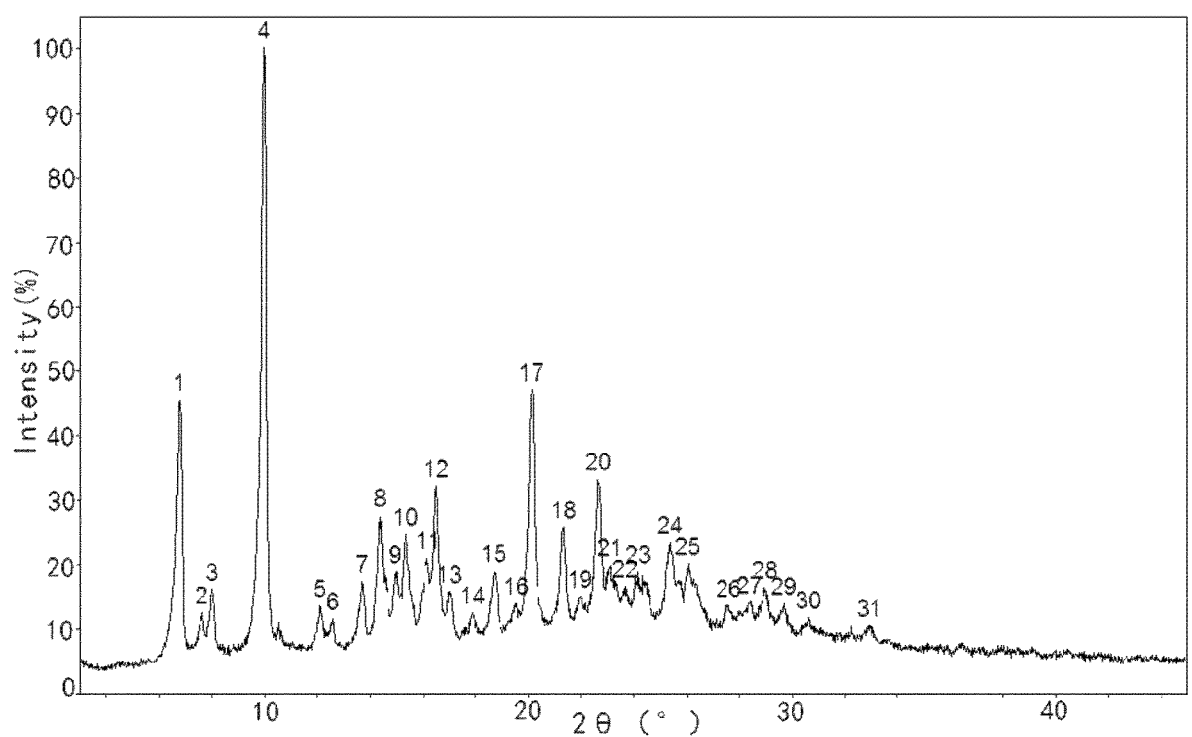
FIG. 1 shows an X-ray powder diffractogram of Form I of compound of Formula A, wherein the horizontal axis (X-axis) plots the diffraction angle 2 theta, and the vertical axis (Y-axis) plots the diffraction intensity (%).

Unless indicated otherwise, the following abbreviations or terms as used in the present application (including the specification and the claims) have the meanings as set forth below. It is to be noted that the singular forms and the articles "a", "an" and "the" in the specification and the claims include plural references, unless clearly indicated otherwise.

The term "crystalline forms of the present invention" as used herein refers to the crystalline forms Form I, Form IV, Form V, Form VI, or Form VIII of compound of Formula A or the solvates thereof, or any mixture thereof. "Form", "crystalline form" and "polymorph" may be used interchangeably herein.

The term "compound of Formula A" or "(S)-4-amino-6-((1-(3-chloro-6-phenylimidazo[1,2-b]pyridazin-7-yl)ethyl) amino)pyrimidine-5-carbonitrile" as used herein refers to a compound having the following chemical structure of Formula A (also referenced as "Compound A"):

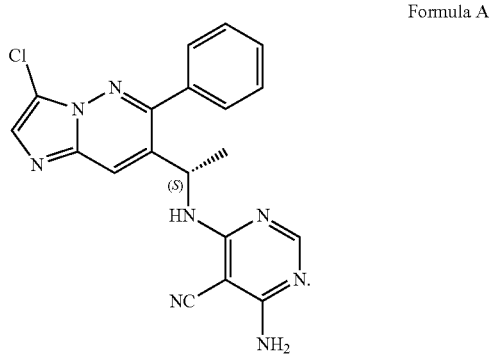

Formula A

The term "$C_{1-6}$ alkanol" as used herein refers to a fully saturated straight or branched alkyl alcohol having 1, 2, 3, 4, 5, or 6 carbon atoms. Examples include but not limited to methanol, ethanol, n-propanol, i-propanol, n-butanol, i-butanol, t-butanol, n-pentanol, i-pentanol, n-hexanol, and the like.

The term "$C_{5-8}$ straight or branched alkane" as used herein refers to a fully saturated straight or branched hydrocarbon having 5, 6, 7, or 8 carbon atoms. Examples include but not limited to n-pentane, n-hexane, n-heptane, n-octane, and the like.

The term "about" as used herein refers to the deviation from a given numerical value of no more than ±10%.

The term "substantially free of other forms" as used herein means that the content of said other forms is less than 50%, preferably less than 40%, preferably less than 30%, preferably less than 20%, preferably less than 10%, preferably less than 5%, preferably less than 1% by weight, based on the total weight of the forms.

The term "solution" as used herein means a mixture of one or more solutes in one or more solvents, for certain use. Solution is intended to encompass homogeneous mixtures as well as heterogeneous mixtures, such as slurries or other suspension mixtures having insoluble (not dissolved) material.

The term "organic solvent" as used herein is broadly intended to mean any appropriate organic solvent for certain use disclosed herein.

The term "dissolution solvent" as used herein refers to any appropriate organic solvent which is capable of dissolving, in whole or in part, the solutes under appropriate conditions, such as an appropriate amount and an appropriate temperature, e.g., room temperature or an elevated temperature.

The term "anti-dissolution solvent" as used herein refers to any appropriate organic solvent in which the substance has less solubility than in the dissolution solvent.

The term "effective amount" of compound of Formula A and the crystalline forms thereof, solvates and the crystalline forms thereof means an amount which is effective in alleviating or improving the diseases responsive to inhibition of $PI_3K$ activity, such as autoimmune diseases, inflammatory diseases, and cancer (preferably hematological malignancy) when administered to an individual, which may be a human, animal or the like, wherein the diseases responsive to inhibition of $PI_3K$ activity, such as autoimmune diseases, inflammatory diseases, and cancer (preferably hematological malignancy) include but not limited to systemic lupus erythematosus, rheumatoid arthritis, multiple sclerosis, allergic rhinitis, chronic obstructive pulmonary disease, psoriasis, asthma, lymphoma (such as Hodgkin's lymphoma, non-Hodgkin's lymphoma, mantle cell lymphoma, follicular lymphoma, small lymphocytic lymphoma, marginal zone lymphoma, Burkitt lymphoma, B cell lymphoma, T cell lymphoma, NK cell lymphoma, and diffuse large B-cell lymphoma), leukemia (such as chronic lymphocytic leukemia, acute lymphocytic leukemia, acute myeloid leukemia, and chronic myelogenous leukemia), multiple myeloma, and Waldenstrom's macroglobulinemia. "Effective amount" may vary with various factors, such as compound, state of disease to be treated, severity of disease to be treated, age and health status of the individual, administration route and form, judgement of the attending physician or a veterinary practitioner, and so on.

The term "individual" or "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but not limited to, birds, and the like. The term "individual" or "subject" does not denote a particular age or sex.

DETAILED DESCRIPTION OF THE INVENTION

The present invention provides novel crystalline forms, solvates and the crystalline forms thereof of compound (S)-4-amino-6-((1-(3-chloro-6-phenylimidazo[1,2-b]pyridazin-7-yl)ethyl) amino)pyrimidine-5-carbonitrile.

The crystalline forms of the present invention have good crystallinity and good stability and are non-hygroscopic. The crystalline forms of the present invention have good reproducibility and can realize repeatable amplified production; moreover, they are stable in ordinary formulations, so it is convenient for them to be used in the manufacture of formulations and treatment of diseases. In addition, the crystalline forms of the present invention have high purity and less solvent residue, which meet the quality requirements of bulk drug, such as ICH Q3A.

The person of ordinary skill in the art can verify the above advantages of the crystalline forms of the present invention according to the test methods disclosed in the pharmacopoeias and the modification thereof, or the conventional methods in the art.

As described herein, the crystalline forms of the present invention may be identified by one or more solid state analytical methods. For example, the crystalline forms of the present invention may be identified by one or more methods, e.g., X-ray powder diffraction, lattice parameters of a single crystal, Fourier Infrared Spectroscopy, differential scanning calorimetry analytical data, and/or a thermogravimetric curve. Moreover, if the identified or analytical result by one of those methods is consistent with that of the forms of the present invention, it does not mean that the result by any other methods is consistent with that of the forms of the present invention.

As described herein, the new crystalline forms may be identified according to X-ray powder diffraction. However, it is known in the art that the peak intensity and/or measured peaks in the X-ray powder diffractogram may vary with the different experiment condition, e.g., different diffraction test conditions and/or preferred orientations or like. Furthermore, the measured 2θ value may be subjected to an error of about ±0.2 2θ due to different instrument precision. However, it is known that, compared with the positions of peaks, the relative intensity values of the peaks more depend on certain properties of the tested samples, e.g., crystal size in the sample, orientation effect of crystalline and purity of the analysed materials. Therefore, the deviation of the peak intensity at about ±20% or greater may occur. However, despite of experimental errors, instrument errors, preferred orientation and the like, one skilled in the art can obtain sufficient information from the XRPD data provided herein to identify Form I and any other crystalline forms of the present invention.

Form I

The present invention provides Form I of compound of Formula A.

In some embodiments, Form I of compound of Formula A may be identified according to X-ray powder diffraction. In some embodiments, the X-ray powder diffraction characteristic diffraction angles (2θ) of Form I of compound of Formula A include 6.8, 10.0, 16.5, 20.1, and 22.6 degrees, the measured 2θ values each having an error of about ±0.2 degrees (2θ).

In some embodiments, the X-ray powder diffraction characteristic diffraction angles (2θ) of Form I of compound of Formula A include 6.8, 10.0, 13.7, 14.4, 15.3, 16.5, 20.1, 21.3, and 22.6 degrees, the measured 2θ values each having an error of about ±0.2 degrees (2θ).

In some embodiments, the X-ray powder diffraction characteristic diffraction angles (2θ) of Form I of compound of Formula A include 6.8, 8.0, 10.0, 12.1, 13.7, 14.4, 15.0, 15.3, 16.5, 18.7, 20.1, 21.3, and 22.6 degrees, the measured 2θ values each having an error of about ±0.2 degrees (2θ).

In some embodiments, the X-ray powder diffraction characteristic diffraction angles (2θ) of Form I of compound of Formula A include 6.8, 7.6, 8.0, 10.0, 12.1, 12.6, 13.7, 14.4, 15.0, 15.3, 16.2, 16.5, 17.0, 18.7, 20.1, 21.3, and 22.6 degrees, the measured 2θ values each having an error of about ±0.2 degrees (2θ).

In some embodiments, the X-ray powder diffraction characteristic diffraction angles (2θ) of Form I of compound of Formula A include 6.8, 7.6, 8.0, 10.0, 12.1, 12.6, 13.7, 14.4, 15.0, 15.3, 16.2, 16.5, 17.0, 17.9, 18.7, 20.1, 21.3, 22.6, 23.1, 25.4, 26.1, and 29.0 degrees, the measured 2θ values each having an error of about ±0.2 degrees (2θ).

In some embodiments, Form I of compound of Formula A has a diffractogram as shown in FIG. 1.

Figure 2:
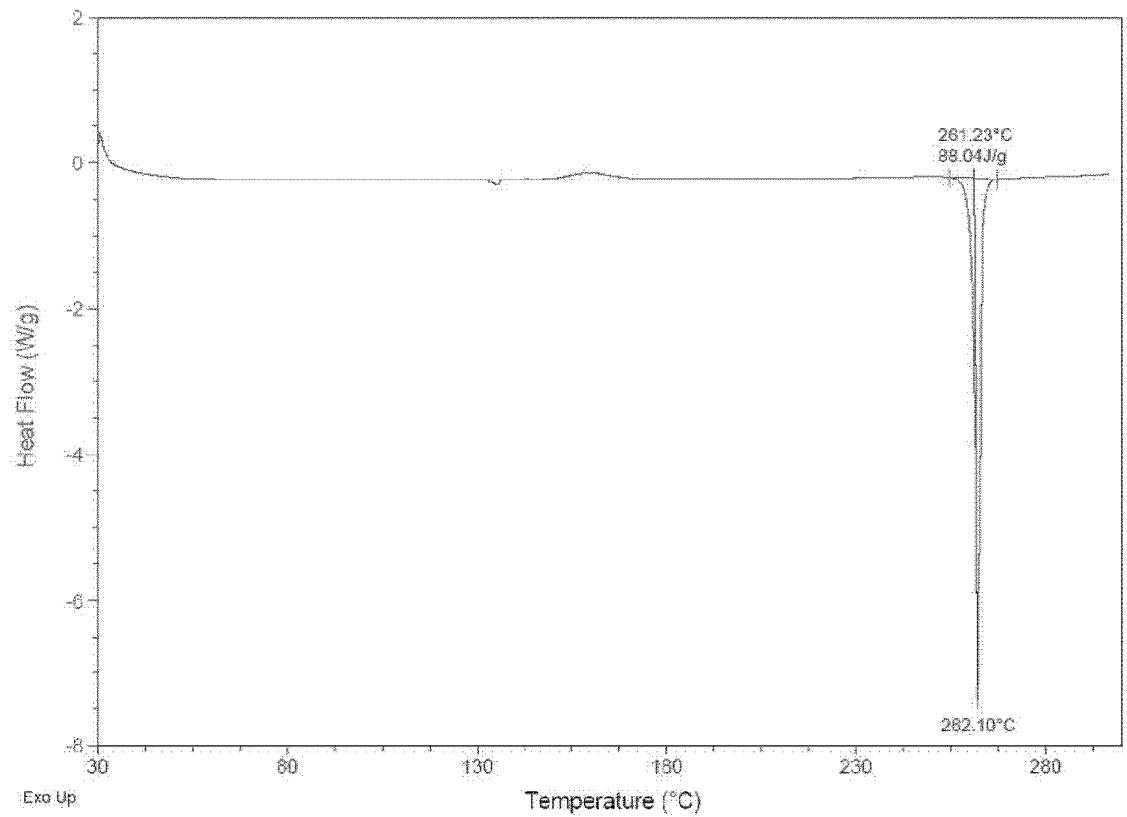
FIG. 2 shows a differential scanning calorimetry (DSC) profile of Form I of compound of Formula A, wherein the horizontal axis (X-axis) plots the temperature (° C.), and the vertical axis (Y-axis) plots the heat flow (mW).

In some embodiments, Form I of compound of Formula A may be characterized by differential scanning calorimetry (DSC). In some embodiments, Form I of compound of Formula A has a DSC curve as shown in FIG. 2. In the DSC profile, the endothermic peak of Form I of compound of Formula A is at about 261.2-262.1° C.

Figure 3:
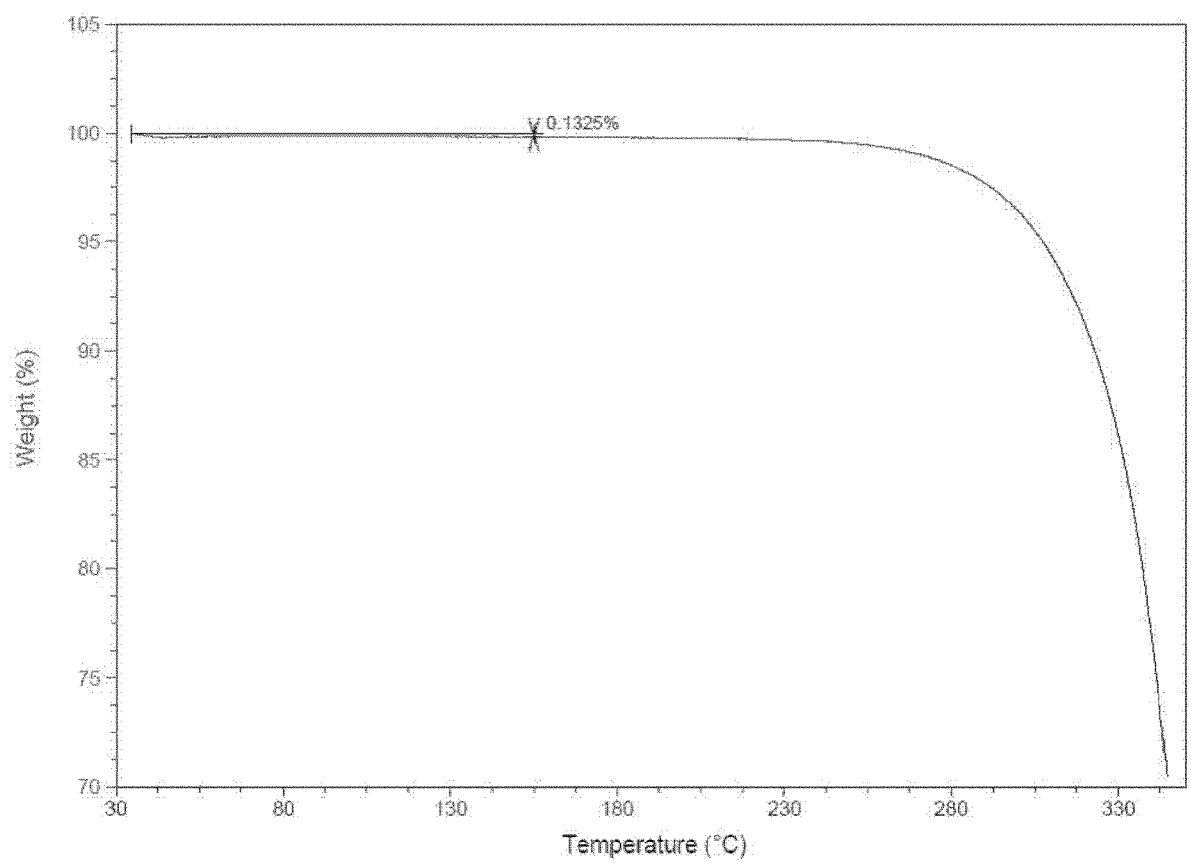
FIG. 3 shows a Thermogravimetric (TG) profile of Form I of compound of Formula A, wherein the horizontal axis (X-axis) plots the temperature (° C.), and the vertical axis (Y-axis) plots the weight percentage (%).

In some embodiments, Form I of compound of Formula A may be characterized by thermogravimetric analysis (TGA). In some embodiments, Form I of compound of Formula A has a TGA curve as shown in FIG. 3, indicating that Form I is an anhydrous material or a neat crystal.

In some embodiments, Form I of compound of Formula A is substantially free of other crystalline forms as described herein. For example, the content by weight of Form I of compound of Formula A is at least 99%, at least 95%, at least 90%, or even lower to 80%. Further, the content by weight of Form I of compound of Formula A is at least 70%, or at least 60%. Even further, the content by weight of Form I of compound of Formula A is at least 50%.

Methods of Preparing Form I

Method A

The present invention relates to a method of preparing Form I of compound of Formula A, comprising:

(1) mixing the compound (S)-4-amino-6-((1-(3-chloro-6-phenylimidazo[1,2-b]pyridazin-7-yl)ethyl)amino)pyrimidine-5-carbonitrile with at least one dissolution solvent, and heating the mixture to reflux to obtain a solution; for example, said at least one dissolution solvent is selected from ethyl acetate, tetrahydrofuran, 1,4-dioxane, butanone, toluene, dichloromethane, a mixture of ethanol and acetic acid, a mixture of ethyl acetate and acetone, a mixture of ethyl acetate and i-propanol, or a mixture of butanone and ethanol;

(2) cooling the solution obtained in step (1) until the solid precipitates;

(3) isolating to obtain the solid Form I of compound of Formula A;

(4) optionally drying the solid obtained in step (3).

In some embodiments, said at least one dissolution solvent is selected from ethyl acetate, tetrahydrofuran, 1,4-dioxane, butanone, toluene, and dichloromethane.

In some embodiments, said at least one dissolution solvent is selected from ethanol/acetic acid (about 25/4 in V/V), ethyl acetate/acetone (from about 7/3 to about 3/7 in V/V), ethyl acetate/i-propanol (from about 7/3 to about 3/7 in V/V), butanone/ethanol (from about 1/1 to about 1/4 in V/V), and the like.

In some embodiments, said cooling the solution may be carried out by cooling slowly while stirring, for example, stirring at a moderate rate, e.g., at a rate ranging from 50 to 200 rpm.

In some embodiments, said cooling the solution may be carried out by cooling naturally or at a controlled temperature to room temperature or lower temperature, such as 25-30° C., 20-25° C., 5-10° C., and the like.

In some embodiments, the drying temperature and drying time can be determined conventionally by one skilled in the art, being appropriate so that the solid is dried sufficiently and the desired crystalline properties are maintained. In some embodiments, the drying temperature is 55-60° C., such as 55° C., 58° C., or 60° C. In some embodiments, the drying time is 1-24 hours, such as 1 hour, 1.5 hours, 2 hours, or 16 hours.

Method B

The present invention provides a further method of preparing Form I of compound of Formula A, comprising:

(1) mixing the compound (S)-4-amino-6-((1-(3-chloro-6-phenylimidazo[1,2-b]pyridazin yl)ethyl)amino)pyrimidine-5-carbonitrile with at least one dissolution solvent or with a mixed solvent consisting of tetrahydrofuran and water, and heating the mixture to reflux to obtain the first solution; for example, said at least one dissolution solvent is selected from one or more of ethyl acetate, 1,4-dioxane, ethanol, and tetrahydrofuran;

(2) adding at least one anti-dissolution solvent into said first solution to obtain the second solution, and then cooling the second solution until the solid precipitates; or alternatively, firstly cooling said first solution, and then adding at least one anti-dissolution solvent until the solid precipitates; provided that, when said dissolution solvent in step (1) is ethanol, the anti-dissolution solvent is not water;

(3) isolating to obtain the solid Form I of compound of Formula A;

(4) optionally drying the solid obtained in step (3).

In some embodiments, said tetrahydrofuran and water are mixed in an appropriate ratio. In some embodiments, the volume ratio of tetrahydrofuran to water is about 4/1.

In some embodiments, said anti-dissolution solvent is selected from water, $C_{5-8}$ straight or branched alkane (such as n-heptane), and isopropyl ether.

In some embodiments, the volume ratio of said at least one dissolution solvent or the mixed solvent consisting of tetrahydrofuran and water to said at least one anti-dissolution solvent ranges from about 1/3 to about 6/1, such as 1/2.7, 1/1.33, 1/1, 1.2/1, 5.4/1.

Method C

The present invention provides a further method of preparing Form I of compound of Formula A, comprising:

(1) suspending the solid of compound (S)-4-amino-6-((1-(3-chloro-6-phenylimidazo[1,2-b] pyridazin-7-yl)ethyl) amino)pyrimidine-5-carbonitrile in a solvent; for example, said solvent is selected from one or more of ethyl acetate, toluene, tetrahydrofuran, and ethanol;

(2) stirring the suspension obtained in step (1), provided that, when said solvent in step (1) is ethanol, the stirring time should not be less than 24 hours;

(3) isolating to obtain the solid Form I of compound of Formula A;

(4) optionally drying the solid obtained in step (3).

In some embodiments, said solid of compound (S)-4-amino-6-((1-(3-chloro-6-phenyl imidazo[1,2-b]pyridazin-7-yl)ethyl)amino)pyrimidine-5-carbonitrile used in step (1) may be in any forms, such as a single crystalline form or amorphous form, e.g., Form IV or Form V, or a mixture of two or more of crystalline forms or amorphous form.

In some embodiments, in said step (1), the compound (S)-4-amino-6-((1-(3-chloro phenylimidazo[1,2-b] pyridazin-7-yl)amino)pyrimidine-5-carbonitrile is not dissolved completely in the suspension system, i.e., part of the compound remains as solid.

In some embodiments, said solvent is selected from one or more of ethyl acetate and toluene.

In some embodiments, heating may be applied in said step (2) when stirring the suspension, and the heating temperature is not higher than the boiling point of the solvent system, such as by heating to reflux.

It is to be understood that, Form I of compound of Formula A may be prepared through one or more of above methods.

Form IV

The present invention provides Form IV of compound of Formula A.

In some embodiments, Form IV of compound of Formula A may be identified according to X-ray powder diffraction. In some embodiments, the X-ray powder diffraction characteristic diffraction angles (2θ) of Form IV of compound of Formula A include 4.6, 9.2, 15.5, 17.8, and 19.0 degrees, the measured 2θ values each having an error of about ±0.2 degrees (2θ).

In some embodiments, the X-ray powder diffraction characteristic diffraction angles (2θ) of Form IV of compound of Formula A include 4.6, 9.2, 11.5, 12.0, 13.2, 15.5, 16.0, 17.8, 19.0, and 22.6 degrees, the measured 2θ values each having an error of about ±0.2 degrees (2θ).

In some embodiments, the X-ray powder diffraction characteristic diffraction angles (2θ) of Form IV of compound of Formula A include 4.6, 9.2, 9.7, 11.3, 11.5, 12.0, 13.2, 13.8, 14.7, 15.5, 16.0, 17.8, 19.0, 22.3, and 22.6 degrees, the measured 2θ values each having an error of about ±0.2 degrees (2θ).

In some embodiments, the X-ray powder diffraction characteristic diffraction angles (2θ) of Form IV of compound of Formula A include 4.6, 7.2, 8.2, 9.2, 9.7, 11.3, 11.5, 12.0, 13.2, 13.8, 14.4, 14.7, 15.5, 16.0, 16.5, 17.8, 19.0, 22.3, and 22.6 degrees, the measured 2θ values each having an error of about ±0.2 degrees (2θ).

In some embodiments, the X-ray powder diffraction characteristic diffraction angles (2θ) of Form IV of compound of Formula A include 4.6, 7.2, 8.2, 9.2, 9.7, 11.3, 11.5, 12.0, 13.2, 13.8, 14.4, 14.7, 15.5, 16.0, 16.5, 17.8, 18.2, 19.0, 19.5, 21.1, 21.6, 22.3, 22.6, and 23.6 degrees, the measured 2θ values each having an error of about ±0.2 degrees (2θ).

Figure 4:
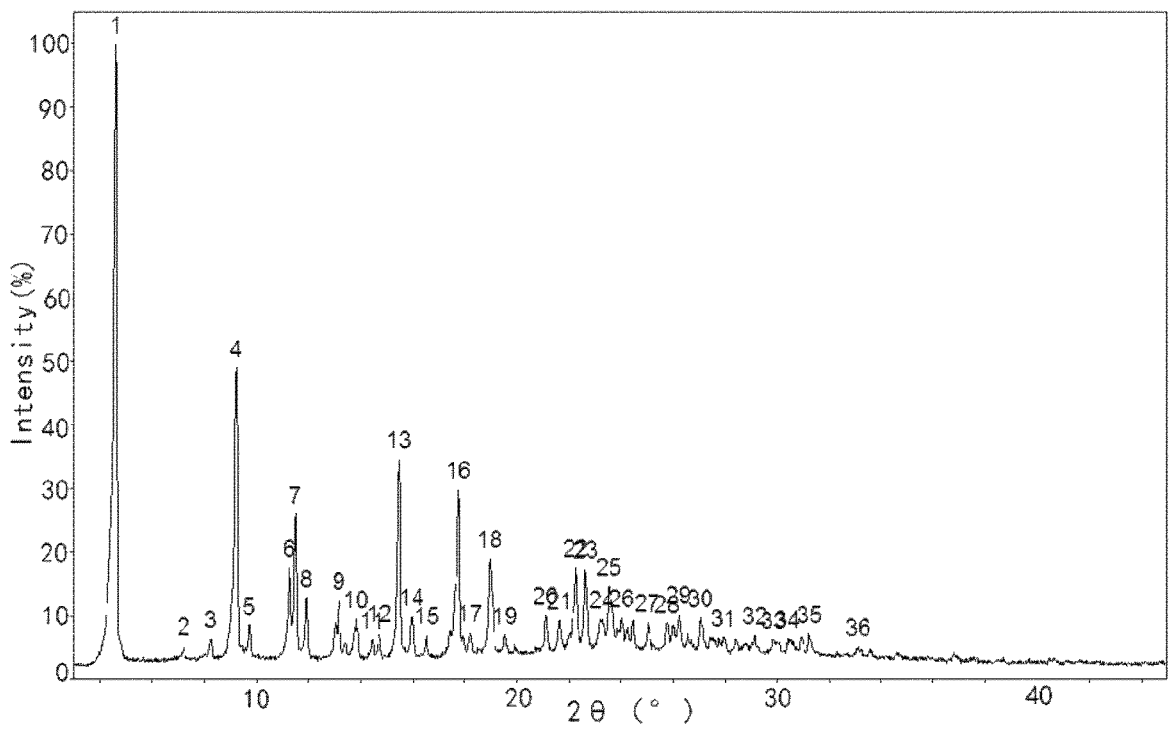
FIG. 4 shows an X-ray powder diffractogram of Form IV of compound of Formula A, wherein the horizontal axis (X-axis) plots the diffraction angle 2 theta, and the vertical axis (Y-axis) plots the diffraction intensity (%).

In some embodiments, Form IV of compound of Formula A has a diffractogram as shown in FIG. 4.

Figure 5:
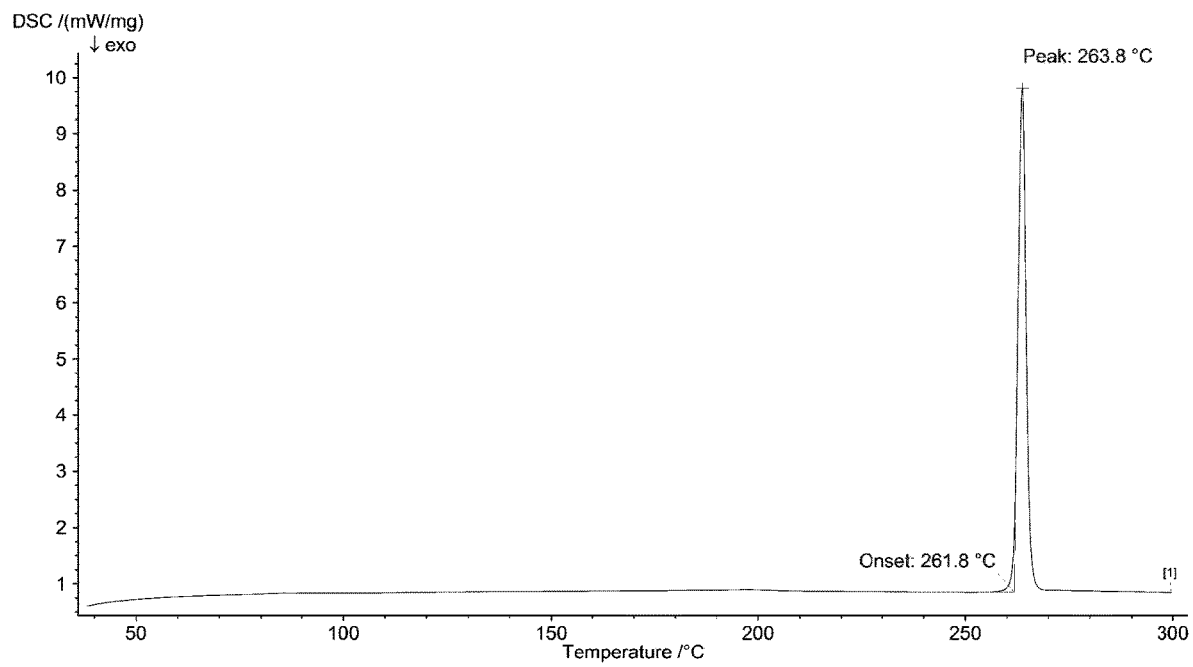
FIG. 5 shows a differential scanning calorimetry (DSC) profile of Form IV of compound of Formula A, wherein the horizontal axis (X-axis) plots the temperature (° C.), and the vertical axis (Y-axis) plots the heat flow (mW).

In some embodiments, Form IV of compound of Formula A may be characterized by differential scanning calorimetry (DSC). In some embodiments, Form IV of compound of Formula A has a DSC curve as shown in FIG. 5. In the DSC profile, the endothermic peak of Form IV of compound of Formula A is at about 261.8-263.8° C.

Figure 6:
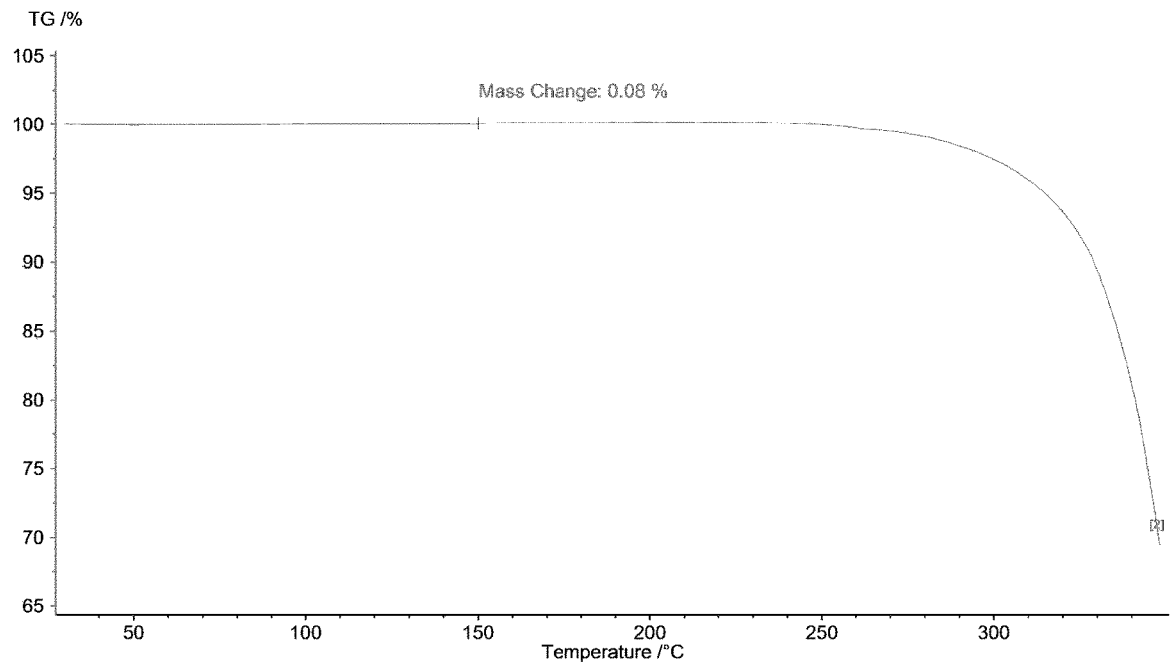
FIG. 6 shows a Thermogravimetric (TG) profile of Form IV of compound of Formula A, wherein the horizontal axis (X-axis) plots the temperature (° C.), and the vertical axis (Y-axis) plots the weight percentage (%).

In some embodiments, Form IV of compound of Formula A may be characterized by thermogravimetric analysis (TGA). In some embodiments, Form IV of compound of Formula A has a TGA curve as shown in FIG. 6, indicating that Form IV is an anhydrous material or a neat crystal.

In some embodiments, Form IV of compound of Formula A is substantially free of other crystalline forms as described herein. For example, the content by weight of Form IV of compound of Formula A is at least 99%, at least 95%, at least 90%, or even lower to 80%. Further, the content by weight of Form IV of compound of Formula A is at least 70%, or at least 60%. Even further, the content by weight of Form IV of compound of Formula A is at least 50%.

Methods of Preparing Form IV
Method A

The present invention relates to a method of preparing Form IV of compound of Formula A, comprising:

(1) mixing the compound (S)-4-amino-6-((1-(3-chloro-6-phenylimidazo[1,2-b]pyridazin-7-yl)ethyl)amino)pyrimidine-5-carbonitrile with at least one dissolution solvent or with a mixed solvent consisting of water-miscible organic solvent and water, and heating the mixture to reflux to obtain a solution; for example, said at least one dissolution solvent is selected from $C_{1-6}$ alkanol, a mixture of i-propanol and acetic acid, or a mixture of methanol and acetic acid; said water-miscible organic solvent is selected from $C_1$-6 alkanol, provided that, said water-miscible organic solvent is not t-butanol;

(2) cooling the solution obtained in step (1) until the solid precipitates;

(3) isolating to obtain the solid Form IV of compound of Formula A;

(4) optionally drying the solid obtained in step (3).

In some embodiments, said $C_{1-6}$ alkanol is selected from methanol, ethanol, i-propanol, and n-butanol. In some embodiments, said $C_{1-6}$ alkanol is selected from methanol, ethanol, and i-propanol. In some embodiments, said $C_{1-6}$ alkanol is selected from ethanol.

In some embodiments, said water-miscible organic solvent is selected from ethanol, i-propanol, and n-butanol.

In some embodiments, the volume percentage of said water-miscible organic solvent in said mixed solvent is not more than about 95%, such as 95%, 90%, 80%, 70%, and the like.

In some embodiments, said at least one dissolution solvent is selected from i-propanol/acetic acid (about 22/1 in V/V), methanol/acetic acid (about 25/3 in V/V), and the like.

In some embodiments, said cooling the solution may be carried out by cooling slowly while stirring, for example, stirring at a moderate rate, e.g., at a rate ranging from 50 to 200 rpm. In some embodiments, stirring is applied after cooling, and the stirring time is preferably not more than 24 hours.

In some embodiments, said cooling the solution may be carried out by cooling naturally or at a controlled temperature (e.g., at a cooling rate of 0.2° C./min, 0.5° C./min, 2° C./min, and the like) to room temperature or lower temperature, such as 20-25° C., 0-5° C., and the like.

In some embodiments, the drying temperature and drying time can be determined conventionally by one skilled in the art, being appropriate so that the solid is dried sufficiently and the desired crystalline properties are maintained. In some embodiments, the drying temperature is 50-60° C., such as 55° C. In some embodiments, the drying time is 1-24 hours, such as 1.5 hours, 2 hours, 5 hours, or 17 hours.

Method B

The present invention provides a further method of preparing Form IV of compound of Formula A, comprising:

(1) mixing the compound (S)-4-amino-6-((1-(3-chloro-6-phenylimidazo[1,2-b]pyridazin-7-yl)ethyl)amino)pyrimidine-5-carbonitrile with at least one dissolution solvent or with a mixed solvent consisting of water-miscible organic solvent and water, and heating the mixture to reflux to obtain the first solution; for example, said at least one dissolution solvent is selected from methanol, ethanol, i-propanol, or a mixture of 1,4-dioxane and ethanol; said water-miscible organic solvent is selected from $C_{1-6}$ alkanol, or a mixture of tetrahydrofuran and ethanol;

(2) adding at least one anti-dissolution solvent into said first solution to obtain the second solution, and then cooling the second solution until the solid precipitates; or alternatively, firstly cooling said first solution, and then adding at least one anti-dissolution solvent until the solid precipitates;

(3) isolating to obtain the solid Form IV of compound of Formula A;

(4) optionally drying the solid obtained in step (3).

In some embodiments, said at least one dissolution solvent is selected from 1,4-dioxane/ethanol (about 1/5 in V/V), and the like.

In some embodiments, said water-miscible organic solvent is selected from $C_{1-6}$ alkanol, such as methanol, ethanol, and i-propanol. In some embodiments, the volume percentage of said water-miscible organic solvent in said mixed solvent consisting of water-miscible organic solvent and water is not more than about 95%, such as 95%, 80%, 70%, and the like.

In some embodiments, said water-miscible organic solvent and water are mixed in an appropriate ratio. In some embodiments, the volume ratio of the water-miscible organic solvent to water ranges from about 6/1 to 4/1, such as methanol/water (about 16/3 in V/V), tetrahydrofuran/ethanol/water (about 1/99/25, about 5/95/25, or about 10/90/25 in V/V).

In some embodiments, said anti-dissolution solvent is selected from water.

In some embodiments, the volume ratio of said at least one dissolution solvent or the mixed solvent consisting of water-miscible organic solvent and water to said at least one anti-dissolution solvent ranges from about 1/3 to about 2/1, such as 1/2.1, 1/1.4, 1/1, 1.36/1.

In some embodiments, said anti-dissolution solvent can be added all in one portion or added in batches.

Method C

The present invention provides a further method of preparing Form IV of compound of Formula A, comprising:

(1) suspending the solid of compound (S)-4-amino-6-((1-(3-chloro-6-phenylimidazo[1,2-b] pyridazin-7-yl)ethyl)amino)pyrimidine-5-carbonitrile in a solvent; wherein, said solvent is selected from $C_{1-6}$ alkanol, water, or a mixed solvent consisting of water-miscible organic solvent (such as those selected from methanol, ethanol, and i-propanol) and water;

(2) stirring the suspension obtained in step (1), provided that, when said solvent in step (1) is ethanol, the stirring time should be less than 24 hours;

(3) isolating to obtain the solid Form IV of compound of Formula A;

(4) optionally drying the solid obtained in step (3).

In some embodiments, said solid of compound (S)-4-amino-6-((1-(3-chloro-6-phenyl imidazo[1,2-b]pyridazin-7-yl)ethyl)amino)pyrimidine-5-carbonitrile used in step (1) may be in any forms, for example a single crystalline form or amorphous form, such as Form I, Form IV, Form V, Form VI, or Form VIII, or a mixture of two or more of crystalline forms or amorphous form.

In some embodiments, in said step (1), the compound (S)-4-amino-6-((1-(3-chloro-6-phenylimidazo[1,2-b] pyridazin-7-yl)ethyl)amino)pyrimidine-5-carbonitrile is not dissolved completely in the suspension system, i.e., part of the compound remains as solid.

In some embodiments, said $C_{1-6}$ alkanol is selected from methanol, ethanol, and i-propanol.

In some embodiments, said water-miscible organic solvent is selected from methanol. In some embodiments, the volume percentage of said water-miscible organic solvent in said mixed solvent is less than about 25%, such as 10%.

In some embodiments, heating may be applied in said step (2) when stirring the suspension, and the heating temperature is not higher than the boiling point of the solvent system, such as 60-70° C., 70-80° C., 75-85° C., and the like. Said heating can facilitate the conversion of the solid in the suspension system to Form IV of compound of Formula A.

It is to be understood that, Form IV of compound of Formula A may be prepared through one or more of above methods.

Form V

The present invention provides Form V of compound of Formula A.

In some embodiments, Form V of compound of Formula A may be identified according to X-ray powder diffraction. In some embodiments, the X-ray powder diffraction characteristic diffraction angles (2θ) of Form V of compound of Formula A include 7.3, 11.6, 14.6, 19.3, and 23.4 degrees, the measured 2θ values each having an error of about ±0.2 degrees (2θ).

In some embodiments, the X-ray powder diffraction characteristic diffraction angles (2θ) of Form V of compound of Formula A include 4.6, 7.3, 8.9, 11.6, 13.5, 14.6, 15.5, 18.0, 19.3, and 23.4 degrees, the measured 2θ values each having an error of about ±0.2 degrees (2θ).

In some embodiments, the X-ray powder diffraction characteristic diffraction angles (2θ) of Form V of compound of Formula A include 4.6, 7.3, 8.9, 10.0, 11.2, 11.6, 13.5, 14.6, 15.5, 16.0, 18.0, 19.3, 20.0, and 23.4 degrees, the measured 2θ values each having an error of about ±0.2 degrees (2θ).

In some embodiments, the X-ray powder diffraction characteristic diffraction angles (2θ) of Form V of compound of Formula A include 4.6, 7.3, 8.9, 10.0, 11.2, 11.6, 13.5, 14.6, 15.5, 16.0, 18.0, 19.3, 20.0, 22.7, 23.4, 25.1, 26.0, and 27.2 degrees, the measured 2θ values each having an error of about ±0.2 degrees (2θ).

In some embodiments, the X-ray powder diffraction characteristic diffraction angles (2θ) of Form V of compound of Formula A include 4.6, 7.3, 8.9, 10.0, 11.2, 11.6, 13.5, 14.6, 15.5, 16.0, 17.7, 18.0, 19.3, 20.0, 22.7, 23.4, 24.0, 25.1, 26.0, 27.2, 28.4, and 29.7 degrees, the measured 2θ values each having an error of about ±0.2 degrees (2θ).

Figure 7:
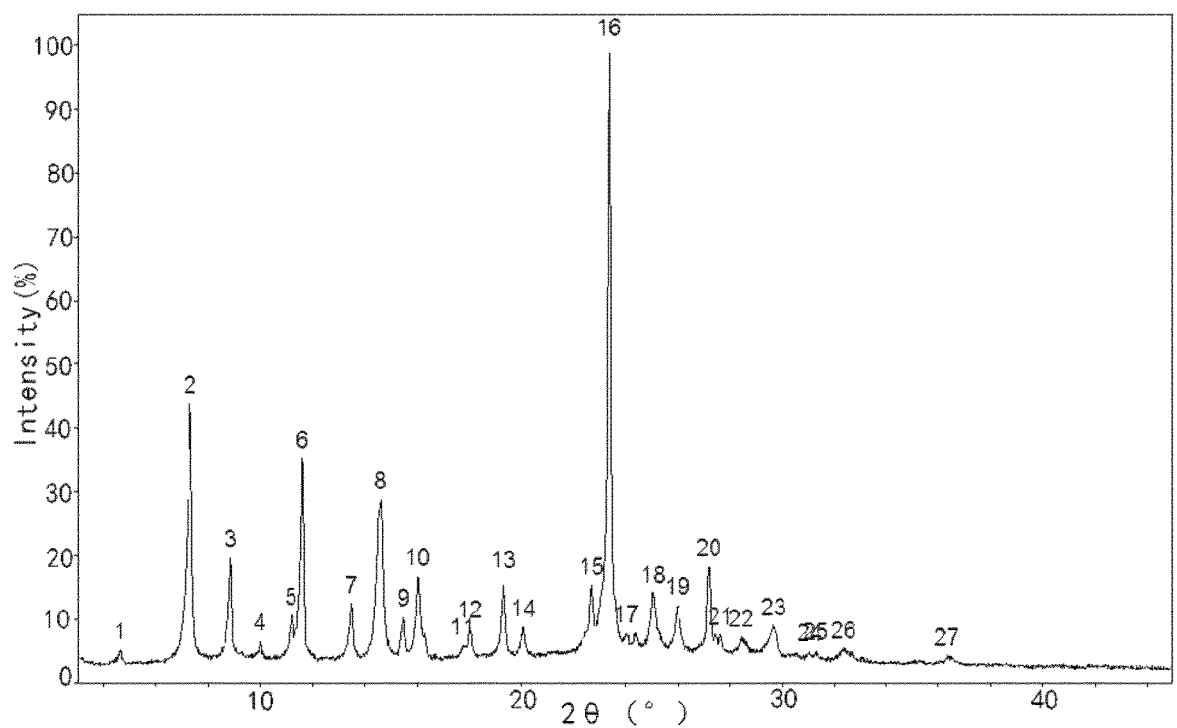
FIG. 7 shows an X-ray powder diffractogram of Form V of compound of Formula A, wherein the horizontal axis (X-axis) plots the diffraction angle 2 theta, and the vertical axis (Y-axis) plots the diffraction intensity (%).

In some embodiments, Form V of compound of Formula A has a diffractogram as shown in FIG. 7.

Figure 8:
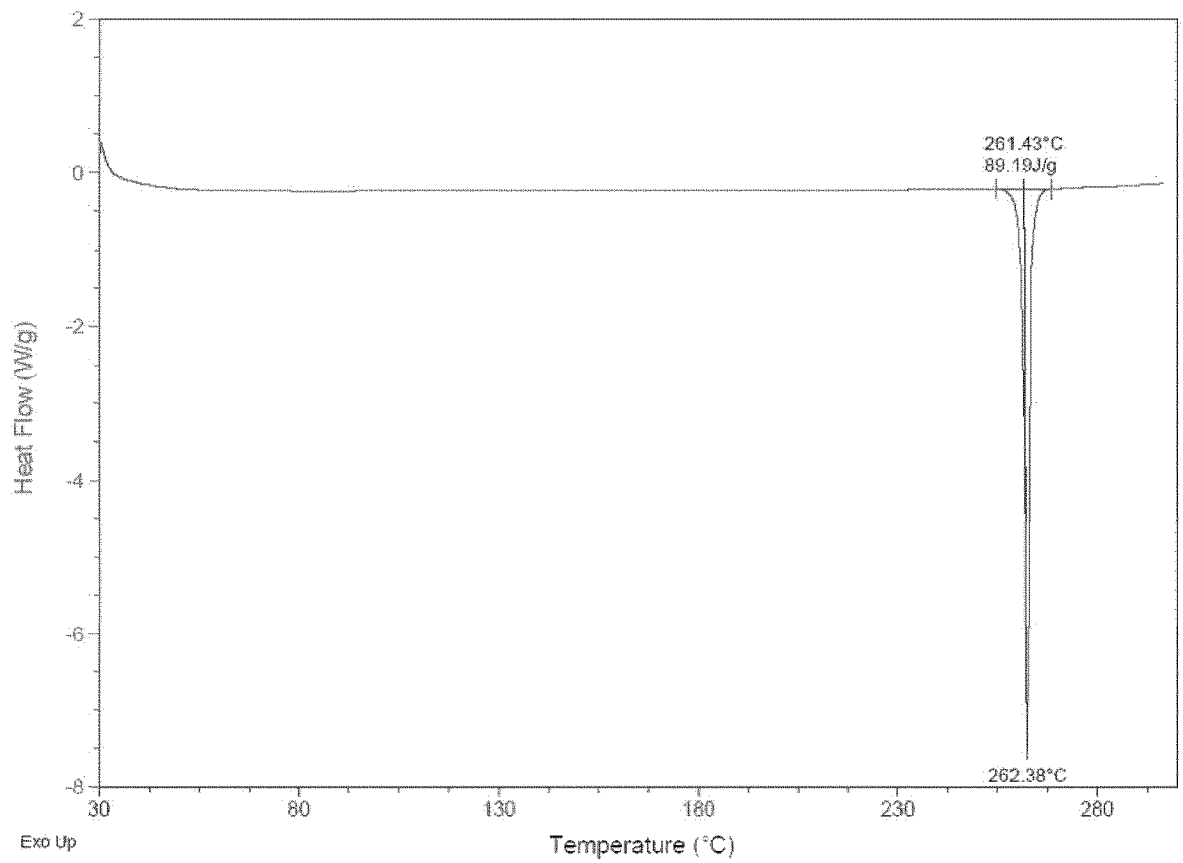
FIG. 8 shows a differential scanning calorimetry (DSC) profile of Form V of compound of Formula A, wherein the horizontal axis (X-axis) plots the temperature (° C.), and the vertical axis (Y-axis) plots the heat flow (mW).

In some embodiments, Form V of compound of Formula A may be characterized by differential scanning calorimetry (DSC). In some embodiments, Form V of compound of Formula A has a DSC curve as shown in FIG. 8. In the DSC profile, the endothermic peak of Form V of compound of Formula A is at about 261.4-262.4° C.

Figure 9:
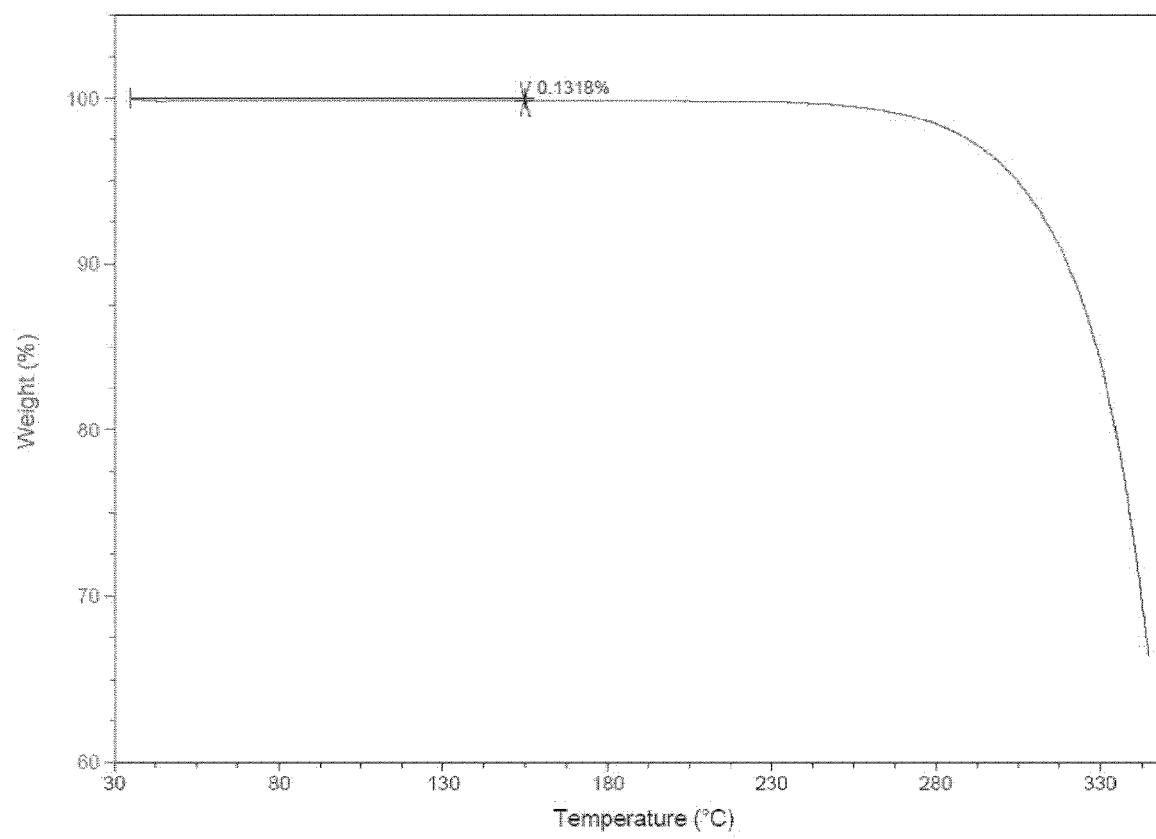
FIG. 9 shows a Thermogravimetric (TG) profile of Form V of compound of Formula A, wherein the horizontal axis (X-axis) plots the temperature (° C.), and the vertical axis (Y-axis) plots the weight percentage (%).

In some embodiments, Form V of compound of Formula A may be characterized by thermogravimetric analysis (TGA). In some embodiments, Form V of compound of Formula A has a TGA curve as shown in FIG. 9, indicating that Form V is an anhydrous material or a neat crystal.

In some embodiments, Form V of compound of Formula A is substantially free of other crystalline forms as described herein. For example, the content by weight of Form V of compound of Formula A is at least 99%, at least 95%, at least 90%, or even lower to 80%. Further, the content by weight of Form V of compound of Formula A is at least 70%, or at least 60%. Even further, the content by weight of Form V of compound of Formula A is at least 50%.

Methods of Preparing Form V
Method A

The present invention relates to a method of preparing Form V of compound of Formula A, comprising:

(1) mixing the compound (S)-4-amino-6-((1-(3-chloro-6-phenylimidazo[1,2-b]pyridazin-7-yl)ethyl)amino)pyrimidine-5-carbonitrile with at least one dissolution solvent or with a mixed solvent consisting of acetonitrile and water, and heating the mixture to reflux to obtain a solution; for example, said at least one dissolution solvent is selected from acetonitrile, a mixture of acetonitrile and acetic acid, a mixture of acetonitrile and ethyl acetate, a mixture of acetonitrile and butanone, a mixture of acetonitrile and tetrahydrofuran, or a mixture of acetone and ethanol;

(2) cooling the solution obtained in step (1) until the solid precipitates;

(3) isolating to obtain the solid Form V of compound of Formula A;

(4) optionally drying the solid obtained in step (3).

In some embodiments, said at least one dissolution solvent is selected from acetonitrile.

In some embodiments, in said mixed solvent consisting of acetonitrile and water, the volume percentage of said acetonitrile in said mixed solvent is 90%.

In some embodiments, said at least one dissolution solvent is selected from acetonitrile/acetic acid (about 14/1 in V/V), acetonitrile/ethyl acetate (about 7/3 in V/V), acetonitrile/butanone (about 1/1 in V/V), acetonitrile/tetrahydrofuran (about 7/3 in V/V), acetone/ethanol (about 1/4 in V/V), and the like.

In some embodiments, said cooling the solution may be carried out by cooling slowly while stirring, for example, stirring at a moderate rate, e.g., at a rate ranging from 50 to 200 rpm.

In some embodiments, said cooling the solution may be carried out by cooling naturally or at a controlled temperature to room temperature or lower temperature, such as 20-25° C., −10--5° C., and the like.

In some embodiments, the drying temperature and drying time can be determined conventionally by one skilled in the art, being appropriate so that the solid is dried sufficiently and the desired crystalline properties are maintained. In some embodiments, the drying temperature is 50-60° C., such as 50° C. or 60° C. In some embodiments, the drying time is 1-24 hours, such as 1 hour or 16 hours.

Method B

The present invention provides a further method of preparing Form V of compound of Formula A, comprising:

(1) suspending the solid of compound (S)-4-amino-6-((1-(3-chloro-6-phenylimidazo[1,2-b] pyridazin-7-yl)ethyl)amino)pyrimidine-5-carbonitrile in acetonitrile;

(2) stirring the suspension obtained in step (1);

(3) isolating to obtain the solid Form V of compound of Formula A;

(4) optionally drying the solid obtained in step (3).

In some embodiments, said solid of compound (S)-4-amino-6-((1-(3-chloro-6-phenyl imidazo[1,2-b]pyridazin-7-yl)ethyl)amino)pyrimidine-5-carbonitrile used in step (1) may be in any forms, for example a single crystalline form or amorphous form, such as Form I, Form IV, or Form V, or a mixture of two or more of crystalline forms or amorphous form.

In some embodiments, in said step (1), the compound (S)-4-amino-6-((1-(3-chloro-6-phenylimidazo[1,2-b] pyridazin-7-yl)ethyl)amino)pyrimidine-5-carbonitrile is not dissolved completely in the suspension system, i.e., part of the compound remains as solid.

In some embodiments, heating may be applied in said step (2) when stirring the suspension, and the heating temperature is not higher than the boiling point of the solvent system, such as 70-80° C.

It is to be understood that, Form V of compound of Formula A may be prepared through one or more of above methods.

Acetone Solvate

The present invention further provides acetone solvate of compound of Formula A.

In some embodiments, acetone solvate of compound of Formula A is monoacetone solvate.

In some embodiments, monoacetone solvate of compound of Formula A is Form VI.

In some embodiments, Form VI of monoacetone solvate of compound of Formula A may be characterized by X-ray powder diffraction. The X-ray powder diffraction characteristic diffraction angles (2θ) of Form VI include 8.6, 10.4, 12.0, 15.0, and 19.7 degrees, the measured 2θ values each having an error of about ±0.2 degrees (2θ).

In some embodiments, the X-ray powder diffraction characteristic diffraction angles (2θ) of Form VI of monoacetone solvate of compound of Formula A include 6.9, 8.6, 9.8, 10.4, 12.0, 13.4, 15.0, 19.7, 20.6, 23.8, and 29.8 degrees, the measured 2θ values each having an error of about ±0.2 degrees (2θ).

In some embodiments, the X-ray powder diffraction characteristic diffraction angles (2θ) of Form VI of monoacetone solvate of compound of Formula A include 6.9, 8.6, 9.8, 10.4, 12.0, 13.4, 15.0, 15.8, 16.8, 18.0, 19.7, 20.6, 23.3, 23.8, 26.2, and 29.8 degrees, the measured 2θ values each having an error of about ±0.2 degrees (2θ).

In some embodiments, the X-ray powder diffraction characteristic diffraction angles (2θ) of Form VI of monoacetone solvate of compound of Formula A include 6.9, 8.6, 9.8, 10.4, 12.0, 13.4, 15.0, 15.8, 16.8, 18.0, 19.4, 19.7, 20.6, 21.0, 22.5, 23.0, 23.3, 23.8, 25.0, 26.2, and 29.8 degrees, the measured 2θ values each having an error of about ±0.2 degrees (2θ).

In some embodiments, the X-ray powder diffraction characteristic diffraction angles (2θ) of Form VI of monoacetone solvate of compound of Formula A include 6.9, 8.6, 9.0, 9.8, 10.4, 12.0, 13.4, 15.0, 15.8, 16.2, 16.8, 17.3, 18.0, 18.2, 18.9, 19.4, 19.7, 20.6, 21.0, 21.6, 22.5, 23.0, 23.3, 23.8, 24.5, 25.0, 26.2, and 29.8 degrees, the measured 2θ values each having an error of about ±0.2 degrees (2θ).

Figure 10:
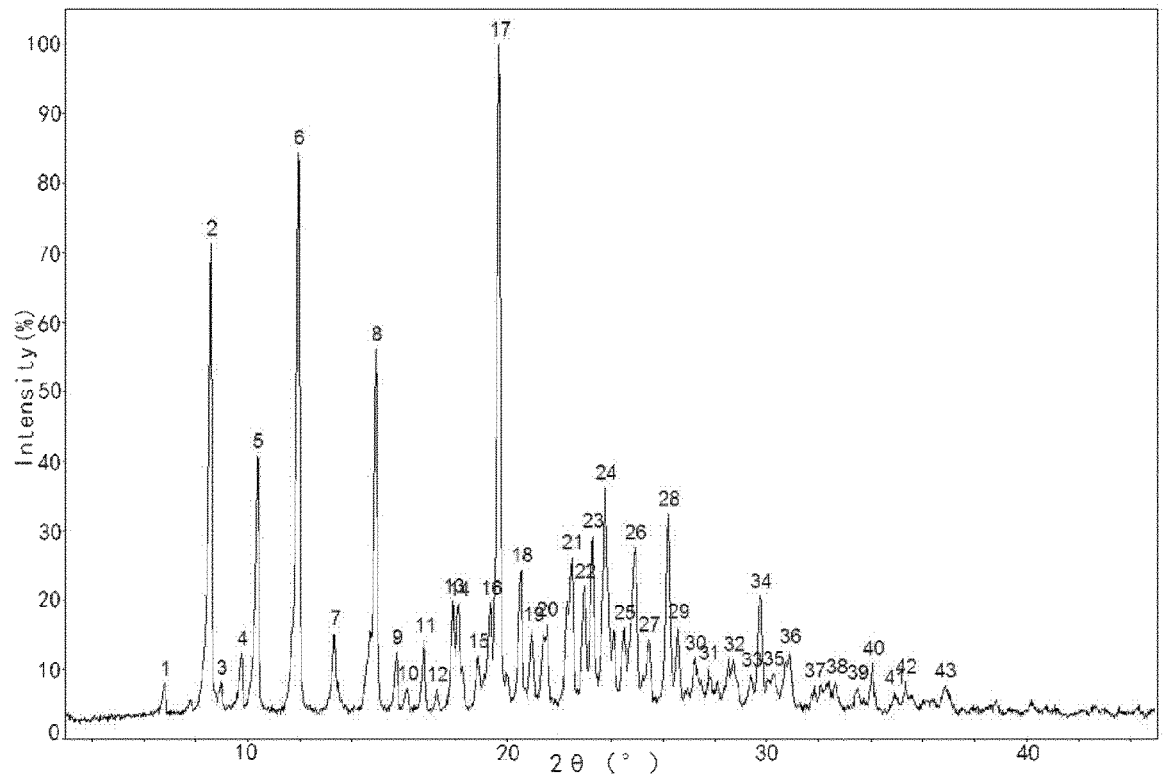
FIG. 10 shows an X-ray powder diffractogram of Form VI of monoacetone solvate of compound of Formula A, wherein the horizontal axis (X-axis) plots the diffraction angle 2 theta, and the vertical axis (Y-axis) plots the diffraction intensity (%).

In some embodiments, Form VI of monoacetone solvate of compound of Formula A has a diffractogram as shown in FIG. 10.

Figure 11:
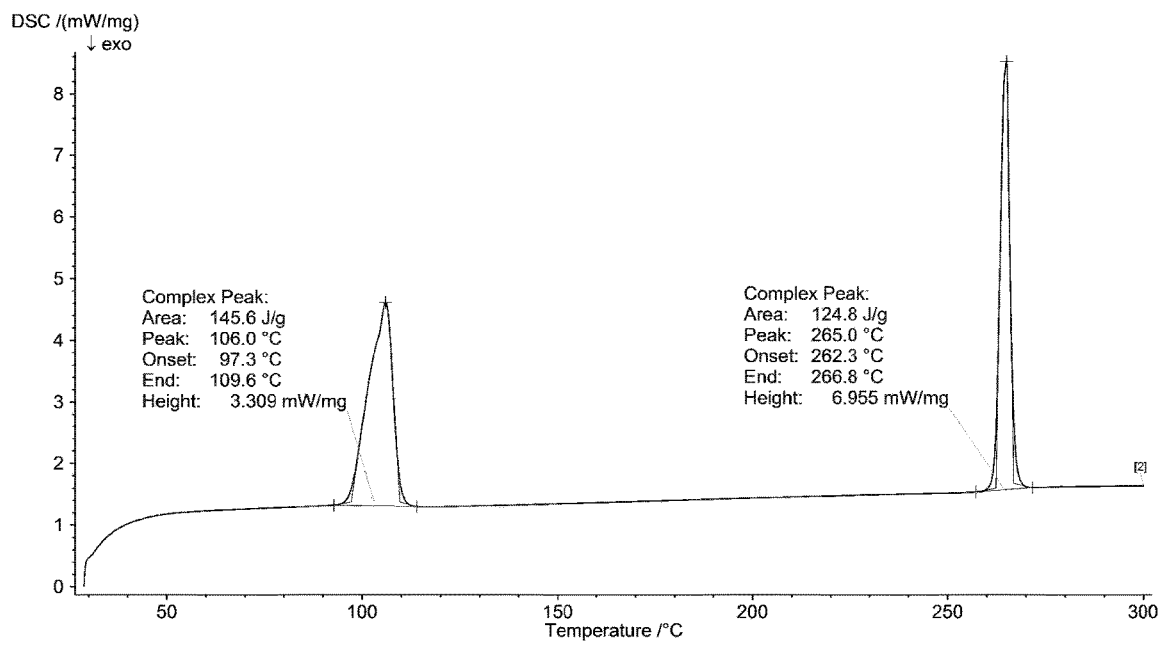
FIG. 11 shows a differential scanning calorimetry (DSC) profile of Form VI of monoacetone solvate of compound of Formula A, wherein the horizontal axis (X-axis) plots the temperature (° C.), and the vertical axis (Y-axis) plots the heat flow (mW).

In some embodiments, Form VI of monoacetone solvate of compound of Formula A may be characterized by differential scanning calorimetry (DSC). In some embodiments, Form VI of monoacetone solvate of compound of Formula A has a DSC curve as shown in FIG. 11. In the DSC profile, the endothermic peaks of Form VI of monoacetone solvate of compound of Formula A are at about 97.3-106.0° C. and about 262.3-265.0° C.

Figure 12:
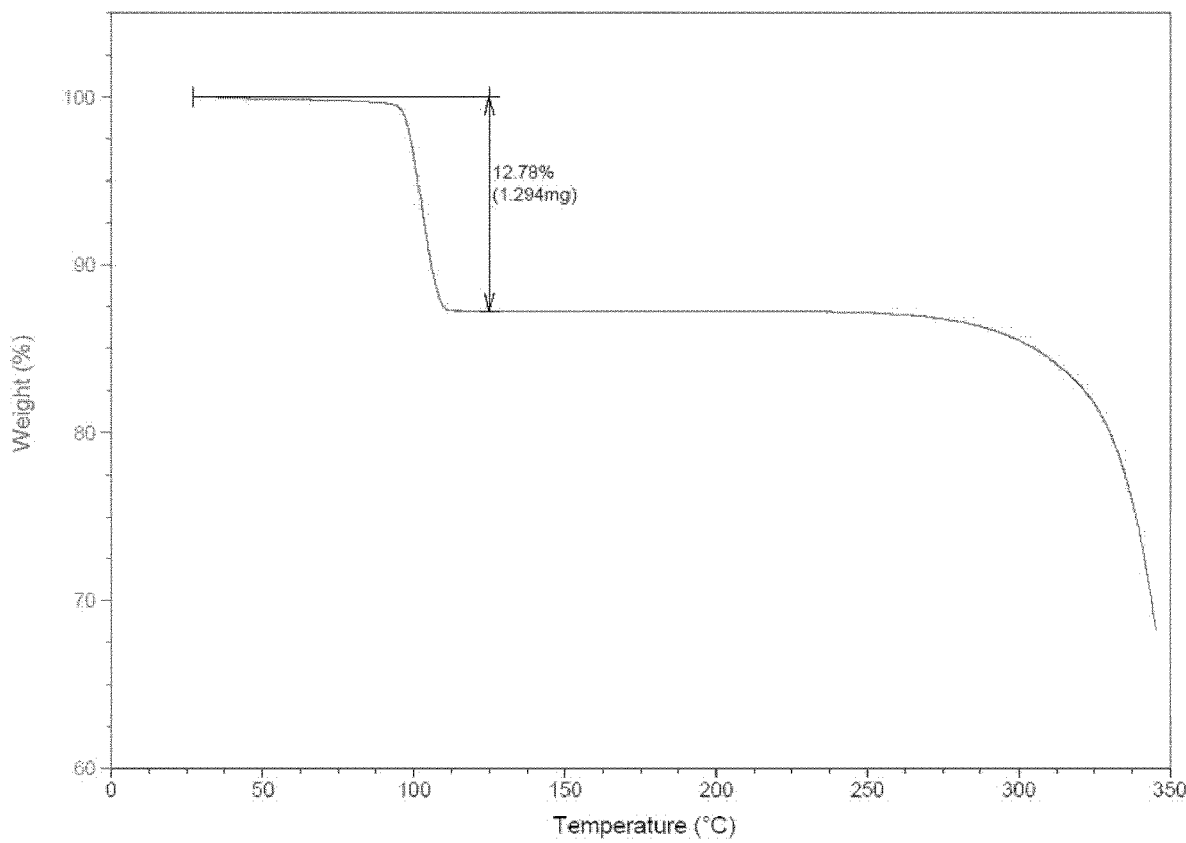
FIG. 12 shows a Thermogravimetric (TG) profile of Form VI of monoacetone solvate of compound of Formula A, wherein the horizontal axis (X-axis) plots the temperature (° C.), and the vertical axis (Y-axis) plots the weight percentage (%).

In some embodiments, Form VI of monoacetone solvate of compound of Formula A may be characterized by thermogravimetric analysis (TGA). In some embodiments, Form VI of monoacetone solvate of compound of Formula A has a TGA curve as shown in FIG. 12, indicating that Form VI is a solvate. The result of further gas chromatography (GC) test shows that the Form contains 1 molecule of acetone. Form VI is a monoacetone solvate.

In some embodiments, Form VI of monoacetone solvate of compound of Formula A is substantially free of other crystalline forms as described herein. For example, the content by weight of Form VI of monoacetone solvate of compound of Formula A is at least 99%, at least 95%, at least 90%, or even lower to 80%. Further, the content by weight of Form VI of monoacetone solvate of compound of Formula A is at least 70%, or at least 60%. Even further, the content by weight of Form VI of monoacetone solvate of compound of Formula A is at least 50%.

Methods of Preparing Form VI

Method A

The present invention relates to a method of preparing Form VI of compound of Formula A, comprising:

(1) mixing the compound (S)-4-amino-6-((1-(3-chloro-6-phenylimidazo[1,2-b]pyridazin-7-yl)ethyl)amino)pyrimidine-5-carbonitrile with at least one dissolution solvent or with a mixed solvent consisting of acetone and water, and heating the mixture to reflux to obtain a solution; wherein, said at least one dissolution solvent is selected from acetone, or a mixed solvent consisting of acetone and i-propanol;

(2) cooling the solution obtained in step (1) until the solid precipitates;

(3) isolating to obtain the solid Form VI of compound of Formula A;

(4) optionally drying the solid obtained in step (3).

In some embodiments, in said mixed solvent consisting of acetone and water, the volume percentage of said acetone in said mixed solvent is 95% or 75%.

In some embodiments, said acetone and i-propanol are mixed in an appropriate ratio. In some embodiments, the volume ratio of acetone to i-propanol is about 7/3.

In some embodiments, said cooling the solution may be carried out by cooling naturally or at a controlled temperature to room temperature or lower temperature, such as 25-30° C., 20-25° C., 0-5° C., and the like.

In some embodiments, the drying temperature and drying time can be determined conventionally by one skilled in the art, being appropriate so that the solid is dried sufficiently and the desired crystalline properties are maintained. In some embodiments, the drying condition is drying in the air for 30 minutes.

Method B

The present invention provides a further method of preparing Form VI of compound of Formula A, comprising:

(1) suspending the solid of compound (S)-4-amino-6-((1-(3-chloro-6-phenylimidazo[1,2-b] pyridazin-7-yl)ethyl) amino)pyrimidine-5-carbonitrile in acetone or a mixed solvent consisting of acetone and water;

(2) stirring the suspension obtained in step (1);

(3) isolating to obtain the solid Form VI of compound of Formula A;

(4) optionally drying the solid obtained in step (3).

In some embodiments, said solid of compound (S)-4-amino-6-((1-(3-chloro-6-phenyl imidazo[1,2-b]pyridazin-7-yl)ethyl)amino)pyrimidine-5-carbonitrile used in step (1) may be in any forms, for example a single crystalline form or amorphous form, such as Form I or Form V, or a mixture of two or more of crystalline forms or amorphous form.

In some embodiments, in said step (1), the compound (S)-4-amino-6-((1-(3-chloro phenylimidazo[1,2-b] pyridazin-7-yl)ethyl)amino)pyrimidine-5-carbonitrile is not dissolved completely in the suspension system, i.e., part of the compound remains as solid.

In some embodiments, said acetone and water are mixed in an appropriate ratio. In some embodiments, the volume ratio of acetone to water is about 3/1.

In some embodiments, in said step (2), the time for stirring the suspension is not less than 48 hours, such as 6 days.

It is to be understood that, Form VI of compound of Formula A may be prepared through one or more of above methods.

Water and i-Propanol Solvate

The present invention further provides water and i-propanol solvate of compound of Formula A.

In some embodiments, water and i-propanol solvate of compound of Formula A contains 3 molecules of water and 0.5 molecule of i-propanol.

In some embodiments, water and i-propanol solvate (containing 3 molecules of water and 0.5 molecule of i-propanol) of compound of Formula A is Form VIII.

In some embodiments, Form VIII of water and i-propanol solvate of compound of Formula A may be characterized by X-ray powder diffraction. The X-ray powder diffraction characteristic diffraction angles (2θ) of Form VIII include 7.0, 8.3, 11.4, 15.3, and 23.1 degrees, the measured 2θ values each having an error of about ±0.2 degrees (2θ).

In some embodiments, the X-ray powder diffraction characteristic diffraction angles (2θ) of Form VIII of water and i-propanol solvate of compound of Formula A include 7.0, 8.3, 9.8, 10.7, 11.4, 15.3, 15.7, 22.4, and 23.1 degrees, the measured 2θ values each having an error of about ±0.2 degrees (2θ).

In some embodiments, the X-ray powder diffraction characteristic diffraction angles (2θ) of Form VIII of water and i-propanol solvate of compound of Formula A include 7.0, 8.3, 9.8, 10.7, 11.4, 13.3, 14.2, 15.3, 15.7, 17.7, 22.4, 23.1, 25.4, and 26.9 degrees, the measured 2θ values each having an error of about ±0.2 degrees (2θ).

In some embodiments, the X-ray powder diffraction characteristic diffraction angles (2θ) of Form VIII of water and i-propanol solvate of compound of Formula A include 7.0, 8.3, 9.8, 10.7, 11.4, 13.3, 13.8, 14.2, 15.3, 15.7, 17.7, 19.0, 19.4, 20.3, 22.4, 23.1, 23.5, 25.4, and 26.9 degrees, the measured 2θ values each having an error of about ±0.2 degrees (2θ).

In some embodiments, the X-ray powder diffraction characteristic diffraction angles (2θ) of Form VIII of water and i-propanol solvate of compound of Formula A include 7.0, 8.3, 9.8, 10.7, 11.4, 13.3, 13.8, 14.2, 15.3, 15.7, 17.7, 19.0, 19.4, 19.6, 20.3, 21.4, 22.4, 23.1, 23.5, 24.0, 25.0, 25.4, 26.9, and 27.2 degrees, the measured 2θ values each having an error of about ±0.2 degrees (2θ).

Figure 13:
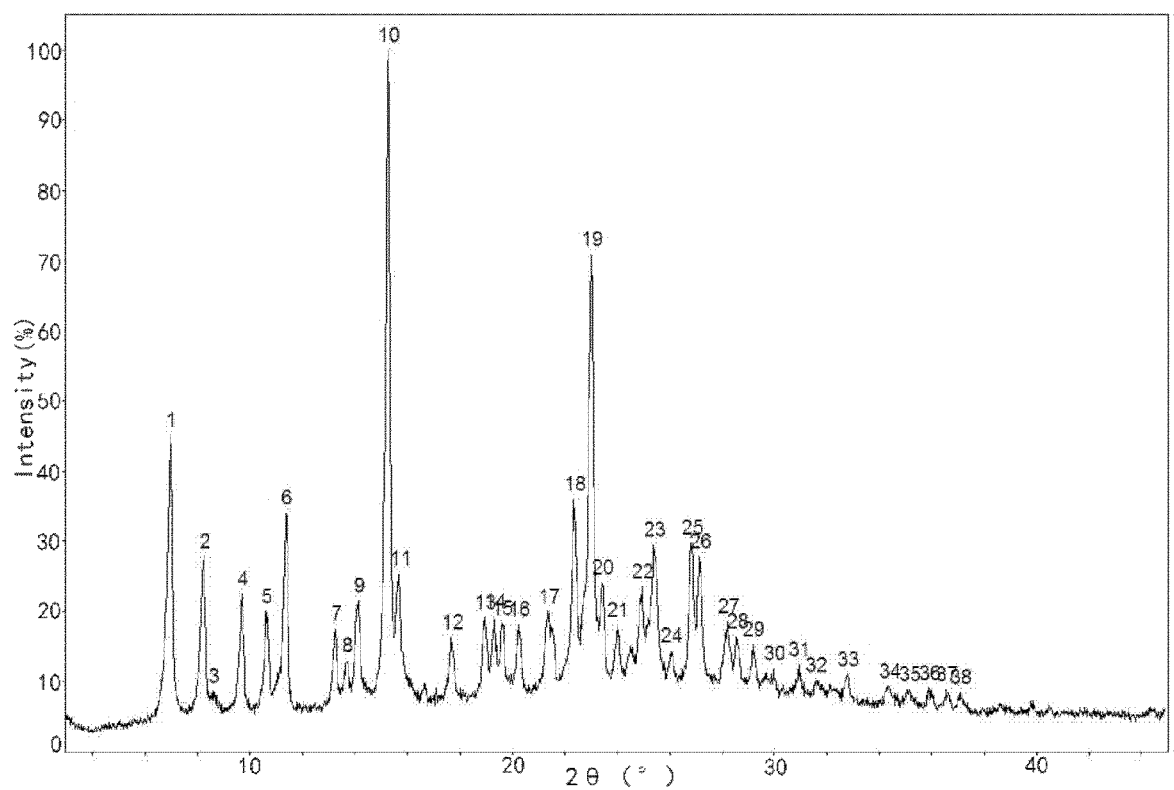
FIG. 13 shows an X-ray powder diffractogram of Form VIII of water and i-propanol solvate of compound of Formula A, wherein the horizontal axis (X-axis) plots the diffraction angle 2 theta, and the vertical axis (Y-axis) plots the diffraction intensity (%).

In some embodiments, Form VIII of water and i-propanol solvate of compound of Formula A has a diffractogram as shown in FIG. 13.

Figure 14:
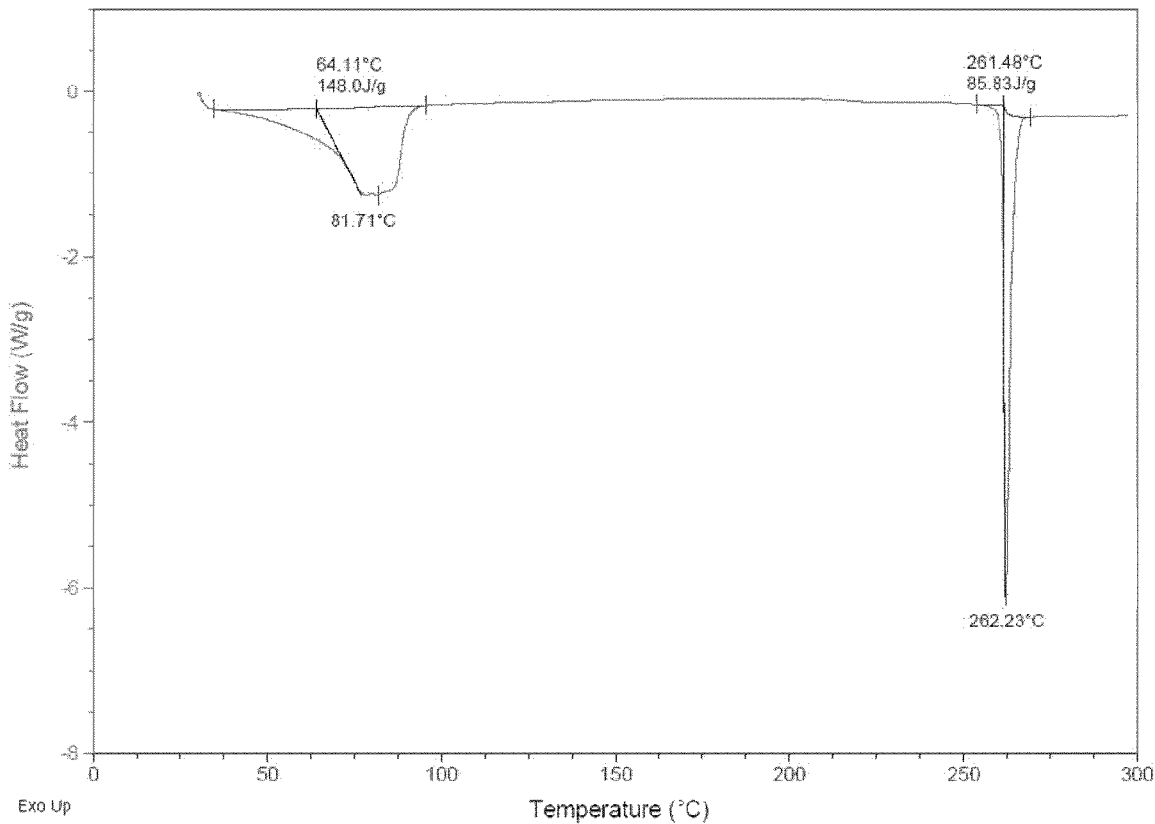
FIG. 14 shows a differential scanning calorimetry (DSC) profile of Form VIII of water and i-propanol solvate of compound of Formula A, wherein the horizontal axis (X-axis) plots the temperature (° C.), and the vertical axis (Y-axis) plots the heat flow (mW).

In some embodiments, Form VIII of water and i-propanol solvate of compound of Formula A may be characterized by differential scanning calorimetry (DSC). In some embodiments, Form VIII of water and i-propanol solvate of compound of Formula A has a DSC curve as shown in FIG. 14. In the DSC profile, the endothermic peaks of Form VIII of water and i-propanol solvate of compound of Formula A are at about 64.1-81.7° C. and about 261.5-262.2° C.

Figure 15:
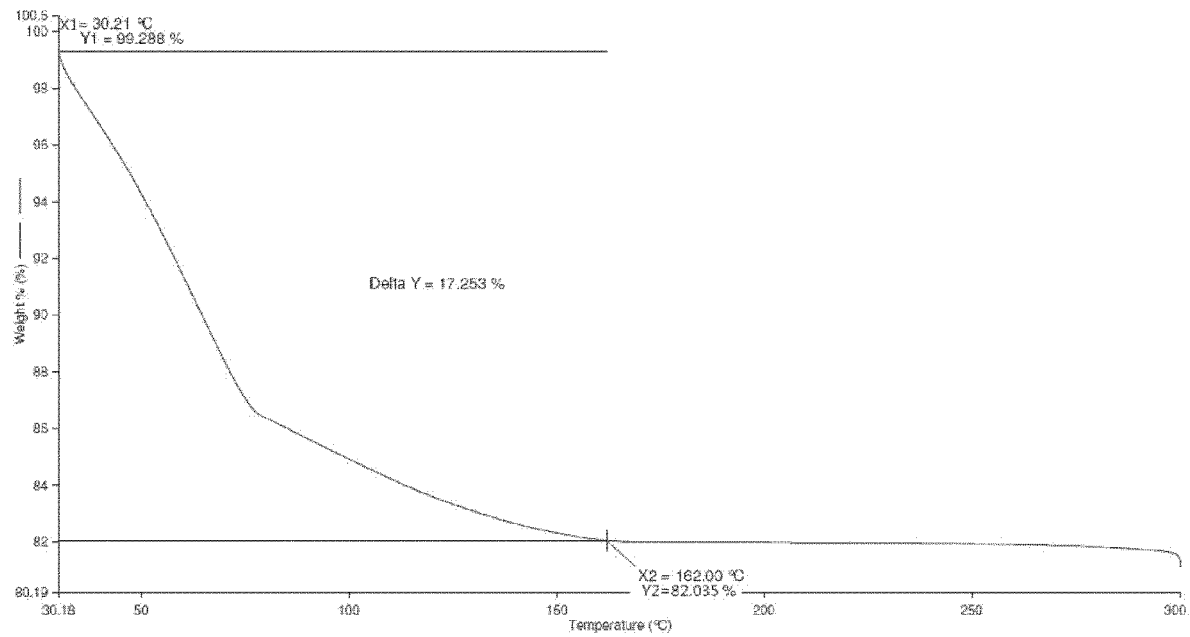
FIG. 15 shows a Thermogravimetric (TG) profile of Form VIII of water and i-propanol solvate of compound of Formula A, wherein the horizontal axis (X-axis) plots the temperature (° C.), and the vertical axis (Y-axis) plots the weight percentage (%).

In some embodiments, Form VIII of water and i-propanol solvate of compound of Formula A may be characterized by thermogravimetric analysis (TGA). In some embodiments, Form VIII of water and i-propanol solvate of compound of Formula A has a TGA curve as shown in FIG. 15, indicating that Form VIII is a solvate. The results of further Karl-Fischer moisture determination (KF) and gas chromatography (GC) test show that the Form contains 3 molecules of water and 0.5 molecule of i-propanol. Form VIII is a water and i-propanol solvate containing 3 molecules of water and 0.5 molecule of i-propanol.

In some embodiments, Form VIII of water and i-propanol solvate of compound of Formula A is substantially free of other crystalline forms as described herein. For example, the content by weight of Form VIII of water and i-propanol solvate of compound of Formula A is at least 99%, at least 95%, at least 90%, or even lower to 80%. Further, the content by weight of Form VIII of water and i-propanol solvate of compound of Formula A is at least 70%, or at least 60%. Even further, the content by weight of Form VIII of water and i-propanol solvate of compound of Formula A is at least 50%.

Methods of Preparing Form VIII

The present invention relates to a method of preparing Form VIII of compound of Formula A, comprising:

(1) mixing the compound (S)-4-amino-6-((1-(3-chloro-6-phenylimidazo[1,2-b]pyridazin yl)ethyl)amino)pyrimidine-5-carbonitrile with a mixed solvent consisting of i-propanol and water, and heating the mixture to reflux to obtain a solution;

(2) cooling the solution obtained in step (1) until the solid precipitates, and then stirring the mixture (preferably for no less than 72 hours);

(3) isolating to obtain the solid Form VIII of compound of Formula A;

(4) optionally drying the solid obtained in step (3).

In some embodiments, in said mixed solvent consisting of i-propanol and water, the volume percentage of said i-propanol in said mixed solvent is 70%.

In some embodiments, the drying temperature and drying time can be determined conventionally by one skilled in the art, being appropriate so that the solid is dried sufficiently and the desired crystalline properties are maintained. In some embodiments, the drying condition is drying in the air for 50-100 minutes.

The features of each embodiment for above methods of preparing the crystalline forms of compound of Formula A or its solvates can be arbitrary combined. Each embodiment obtained from such arbitrary combinations is included within the scope of the present invention, as if these embodiments obtained from such arbitrary combinations are specifically and individually listed herein.

Pharmaceutical Compositions and Methods of Treatment

The crystalline forms of compound of Formula A, the solvates of compound of Formula A and the crystalline forms thereof (such as Form I, Form IV, Form V, Form VI, and Form VIII) are useful in the treatment of diseases, such as autoimmune diseases, inflammatory diseases, and cancer. The cancer is preferably hematological malignancy. The autoimmune diseases, inflammatory diseases, and cancer include but not limited to systemic lupus erythematosus, rheumatoid arthritis, multiple sclerosis, allergic rhinitis, chronic obstructive pulmonary disease, psoriasis, asthma, lymphoma (such as Hodgkin's lymphoma, non-Hodgkin's lymphoma, mantle cell lymphoma, follicular lymphoma, small lymphocytic lymphoma, marginal zone lymphoma, Burkitt lymphoma, B cell lymphoma, T cell lymphoma, NK cell lymphoma, and diffuse large B-cell lymphoma), leukemia (such as chronic lymphocytic leukemia, acute lymphocytic leukemia, acute myeloid leukemia, and chronic myelogenous leukemia), multiple myeloma, and Waldenstrom's macroglobulinemia.

The present invention provides the method of treating diseases responsive to inhibition of $PI_3K$ activity, comprises administering the active pharmaceutical ingredients comprising compound of Formula A, or one or more of the crystalline forms of compound of Formula A, the solvates of compound of Formula A and the crystalline forms thereof (such as Form I, Form IV, Form V, Form VI, or Form VIII).

In some embodiments, the treatment method is directed to at least one disease responsive to inhibition of $PI_3K$ activity, such as autoimmune diseases, inflammatory diseases, and cancer (preferably hematological malignancy). An effective amount of a pharmaceutical composition of the present invention is administered to a subject in need thereof, wherein the pharmaceutical composition comprises at least one pharmaceutically acceptable carrier and one or more of the crystalline forms of compound of Formula A, the solvates of compound of Formula A and the crystalline forms thereof (such as Form I, Form IV, Form V, Form VI, or Form VIII).

The dosing amount of the at least one active pharmaceutical ingredient selected from the crystalline forms of compound of Formula A, the solvates of compound of Formula A and the crystalline forms thereof (such as Form I, Form IV, Form V, Form VI, or Form VIII) to achieve the desired biological effect may depend on a number of factors, e.g., the intended use, the mode of administration, and the clinical condition of the patient. The daily dose may, for example, range from 0.01 mg to 3 g/day (such as from 0.05 mg to 2 g/day, even from 100 mg to 1 g/day). Unit dose formulations which can be administered orally include, for example, tablets or capsules.

For the therapy of the above-mentioned conditions, the at least one active pharmaceutical ingredient selected from the crystalline forms of compound of Formula A, the solvates of compound of Formula A and the crystalline forms thereof may be administered as such, but typically in the form of a pharmaceutical composition formulated with one or more pharmaceutically acceptable carriers or excipients.

Representative carriers or excipients should be compatible with the other ingredients of the composition and do not have harmful effect on the patient's health. The carrier or excipient may be a solid or a liquid or both, and may be formulated with the crystalline forms of compound of Formula A, the solvates of compound of Formula A and the crystalline forms thereof (such as Form I, Form IV, Form V, Form VI, and/or Form VIII) into a pharmaceutical composition or a unit dosage form (for example, a tablet, a capsule), which may contain from 0.05% to 95% by weight of the crystalline forms of compound of Formula A, the solvates of compound of Formula A or the crystalline forms thereof. The pharmaceutical compositions described herein can be produced by known pharmaceutical formulating methods, such as those involving mixing with pharmaceutically acceptable carriers and/or excipients and diluents.

In some embodiments, the at least one active pharmaceutical ingredient selected from the crystalline forms of compound of Formula A, the solvates of compound of Formula A and the crystalline forms thereof (such as Form I, Form IV, Form V, Form VI, and Form VIII) may be combined with at least one component, such as carrier and/or excipient and/or diluent, which may be selected from sweeteners, flavoring agents, coloring agents, dyes, and emulsifiers.

In some embodiments, the conversion of the crystalline forms of compound of Formula A, the solvates of compound of Formula A and the crystalline forms thereof (such as Form I, Form IV, Form V, Form VI, and Form VIII) will not occur when formulating with the one or more pharmaceutically acceptable carriers and/or excipients and/or diluents. In other embodiments, the crystalline forms of compound of Formula A, the solvates of compound of Formula A and the crystalline forms thereof (such as Form I, Form IV, Form V, Form VI, or Form VIII) may be converted, in whole or in part, to one or more other crystalline forms or amorphous form, or to a non-solid form, when formulating with the one or more pharmaceutically acceptable carriers and/or excipients and/or diluents. In some embodiments, Form I or other crystalline forms described herein can be dissolved when formulated into a pharmaceutical composition. Accordingly, in such "dissolved" cases, Form I or other crystalline forms no longer exists in their respective forms in the pharmaceutical composition.

In some embodiments, the at least one active pharmaceutical ingredient selected from the crystalline forms of compound of Formula A, the solvates of compound of Formula A and the crystalline forms thereof (such as Form I, Form IV, Form V, Form VI, and Form VIII) is formulated into a suitable dosage form.

Pharmaceutical compositions described herein may be dosage forms suitable for oral and peroral (for example sublingual) administration. The suitable mode of administration may depend on not only the condition in each individual case and severity of the condition to be treated, but also the nature of the specific forms of the active pharmaceutical ingredient selected from the crystalline forms of compound of Formula A, the solvates of compound of Formula A and the crystalline forms thereof (such as Form I, Form IV, Form V, Form VI, and Form VIII) used in preparing the pharmaceutical composition.

Suitable pharmaceutical compositions for oral administration prepared from the at least one active pharmaceutical ingredient selected from the crystalline forms of compound of Formula A, the solvates of compound of Formula A and the crystalline forms thereof (such as Form I, Form IV, Form V, Form VI, and Form VIII) may be in the form of unit dosage forms such as capsules, cachets, and tablets, including suckable tablets, each of which is prepared with a defined amount of the at least one active pharmaceutical ingredient described herein; as well as in the forms selected from powders, granules, solutions, suspensions in an aqueous or nonaqueous liquid, and oil-in-water and water-in-oil emulsions. Those compositions may, as already mentioned, be prepared by any suitable pharmaceutical formulation methods, such as those including a step wherein the at least one active pharmaceutical ingredient selected from the crystalline forms of compound of Formula A, the solvates of compound of Formula A and the crystalline forms thereof (such as Form I, Form IV, Form V, Form VI, and Form VIII) and a carrier and/or excipient and/or diluent (which may consist of one or more added ingredients) are combined. The compositions can generally be produced by uniformly and homogeneously mixing the at least one active pharmaceutical ingredient selected from the crystalline forms of compound of Formula A, the solvates of compound of Formula A and the crystalline forms thereof (such as Form I, Form IV, Form V, Form VI, and Form VIII) with liquid or finely divided solid carriers, after which the product can be shaped.

The at least one active pharmaceutical ingredient selected from the crystalline forms of compound of Formula A, the solvates of compound of Formula A and the crystalline forms thereof (such as Form I, Form IV, Form V, Form VI, and Form VIII) can also be administered in combination with one or more other active ingredients (such as in the synergetic therapy). When administered as a combination, the active ingredients can be formulated as separate compositions that are administered at the same time or sequentially at different times (such as administered sequentially in any orders) through the same or different administration routes, or the active ingredients can be administered in the same pharmaceutical composition.

In some embodiments, the at least one active pharmaceutical ingredient selected from the crystalline forms of compound of Formula A, the solvates of compound of Formula A and the crystalline forms thereof (such as Form I, Form IV, Form V, Form VI, and Form VIII) can be administered in combination with one or more other active ingredients with known therapeutical effect, for example for the treatment of diseases responsive to inhibition of $PI_3K$ activity, such as autoimmune diseases, inflammatory diseases, and cancer (preferably hematological malignancy).

The phrase "combination", as described herein, defines the combined use of the at least one active pharmaceutical ingredient selected from the crystalline forms of compound of Formula A, the solvates of compound of Formula A and the crystalline forms thereof (such as Form I, Form IV, Form V, Form VI, and Form VIII) with one or more other active ingredients, such as, the combined use in the treatment of autoimmune diseases or inflammatory diseases (for example, in combination with immunosuppressants, steroids), the combined use in the treatment of cancer, especially hematological malignancy (for example, in combination with BTK inhibitors, SYK inhibitors, JAK inhibitors, Bcl-2 inhibitors, anti-CD20 monoclonal antibodies, Lenalidomide). Examples of BTK inhibitors include but not limited to Ibrutinib, ACP-196 (Acalabrutinib), CC-292 (Spebrutinib), ONO-4059 (Tirabrutinib), BGB-3111, and GDC-0853. Examples of SYK inhibitors include but not limited to GS-9973 (Entospletinib) and HMPL-523. Examples of JAK inhibitors include but not limited to Ruxolitinib. Examples of Bcl-2 inhibitors include but not limited to Venetoclax (ABT-199), ABT-263 (Navitoclax), and BCL201 (S55746). Examples of anti-CD20 monoclonal antibodies include but not limited to Rituximab, Ofatumumab, and Obinutuzumab.

Examples of immunosuppressants include but not limited to corticoids (e.g., fluticasone propionate, beclomethasone dipropionate, mometasone furoate, triamcinolone acetonide, or budesonide), disease-modifying agents (e.g., antimalarials, methotrexate, sulfasalazine, mesalamine, azathioprine, 6-mercaptopurine, metronidazole, or D-penicillamine), non-steroidal anti-inflammatory drugs (e.g., acetominophen, aspirin, sodium salicylate, sodium cromoglycate, magnesium salicylate, choline magnesium salicylate, salicylsalicylic acid, ibuprofen, naproxen, diclofenac, diflunisal, etodolac, fenoprofen calcium, flurbiprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, or tolmetin), COX-2 inhibitors, inhibitors of cytokine synthesis/release (e.g., anti-cytokine antibodies, anti-cytokine receptor antibodies, and the like).

Examples of steroids include but not limited to glucocorticoids, such as budesonide, beclomerthasone dipropionate, fluticasone propionate, ciclesonide, mometasone furoate, and the like.

In addition, the at least one active pharmaceutical ingredient selected from the crystalline forms, the solvates and the crystalline forms thereof of the present invention can also be used in combination with other anti-neoplastic agents. As used herein, the term "anti-neoplastic agent" refers to any agent that is useful for treating the cancer. Examples of anti-neoplastic agent include but not limited to: radiotherapy agent, immunotherapy agent, DNA damaging chemotherapeutic agents, and chemotherapeutic agents that disrupt cell replication.

DNA damaging chemotherapeutic agents include but not limited to, for example, topoisomerase I inhibitors (e.g., irinotecan, topotecan, camptothecin and analogs or metabolites thereof, and adriacin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, dacarbazine, methotrexate, mitomycin, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitabine, gemcitabine, fludarabine, cytarabine, azacitidine, mercaptopurine, thioguanine, pentostatin, and hydroxyurea).

Chemotherapeutic agents those disrupt cell replication include but not limited to: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby down-regulate cell replication (e.g., trastuzumab, rituximab, cetuximab, and bevacizumab); and other inhibitors of proteins or enzymes known to be upregulated, over-expressed, or activated in cancers, the inhibition of which can down-regulates cell replication.

Furthermore, methods described herein are not limited by the sequence of administration; the one or more other active ingredients may be administered simultaneously to, prior to or after the administration of the at least one active pharmaceutical ingredient. The at least one active pharmaceutical ingredient in the combination described above is selected from the crystalline forms of compound of Formula A, the solvates of compound of Formula A and the crystalline forms thereof (such as Form I, Form IV, Form V, Form VI, and Form VIII).

The following non-limiting examples are provided.

Experiments

The compound (S)-4-amino-6-((1-(3-chloro-6-phenylimidazo[1,2-b]pyridazin-7-yl)ethyl) amino)pyrimidine-5-carbonitrile raw material used in the examples were prepared according to WO2016045591A1.

All reagents, except intermediates, used in this disclosure are commercially available. The names of all compounds, except the reagents, were generated by ChemDraw Professional 16.0.

Unless otherwise indicated, X-ray powder diffractograms were obtained using Germany Bruker D8 ADVANCE X-ray diffractometer (target: Cu; voltage: 40 kV; electric current: 40 mA; scanning speed: 4 degrees/min; step size: 0.02 degree; scanning range: 3-45 degrees).

Unless otherwise indicated, differential scanning calorimetry (DSC) was performed on Germany NETZSCH DSC 204F1 (purge gas: nitrogen; flow rate: 20-60 mL min$^{-1}$; heating rate: 5-10° C./min; temperature range: 30° C. to 300° C.). The samples were measured in the pricked aluminum pans. Indium was used for temperature calibration. Alternatively, DSC was performed on DSC Q2000 of American TA company.

Unless otherwise indicated, thermogravimetric (TG) analyses were obtained using Germany NETZSCH TGA 209F1 (purge gas: nitrogen; heating rate: 10° C./min); or were obtained using TG Q500 of American TA company.

Example 1 Preparation of Form I of Compound of Formula A 0.86 g of compound of Formula A was dissolved in 28 mL of ethyl acetate under heating and stirring. Then the solution was cooled to room temperature and stirred for 17 hours at a moderate rate. Then the precipitate was filtered and dried at 60° C. under vacuum for 1.5 hours to give 0.53 g of solid.

The obtained powder sample is Form I of compound of Formula A, the X-ray powder diffractogram of which is shown in FIG. 1. Peaks (2θ) chosen from the figure have the following values: 6.8, 7.6, 8.0, 10.0, 12.1, 12.6, 13.7, 14.4, 15.0, 15.3, 16.2, 16.5, 17.0, 17.9, 18.7, 20.1, 21.3, 22.6, 23.1, 25.4, 26.1, and 29.0 degrees, the measured 2θ values each having an error of about ±0.2 degrees (2θ), wherein characteristic peaks (2θ) are at 6.8, 10.0, 16.5, 20.1, and 22.6 degrees. DSC result is given in FIG. 2, showing that the endothermic peak of Form I is at about 261.2-262.1° C.

Example 2 Preparation of Form I of Compound of Formula A

An appropriate amount of compound of Formula A were suspended in an appropriate amount of the solvents listed in Table 1 respectively. The suspensions were heated to the temperatures listed in Table 1 to dissolve. Then the solutions were cooled to 20-25° C. Then the precipitates were filtered respectively to give each sample. Upon measurement, the X-ray powder diffractogram of each of the obtained samples is consistent with that of Form I of compound of Formula A obtained in Example 1.

TABLE 1

| Amount of compound of Formula A/solvent | Solvent | Heating temperature |
|---|---|---|
| 150 mg/1.2 mL | 1,4-dioxane | 80-85° C. |
| 150 mg/1.5 mL | tetrahydrofuran | 60-70° C. |
| 80 mg/1.16 L | ethanol/acetic acid (volume ratio 25/4) | 75-80° C. |

Example 3 Preparation of Form I of Compound of Formula A

An appropriate amount of compound of Formula A were suspended in an appropriate amount of the solvents listed in Table 2 respectively. The suspensions were heated to the temperatures listed in Table 2 to dissolve. Then the solutions were cooled to 20-25° C. and stirred for a period of time at a moderate rate. Then the precipitates were filtered respectively to give each sample. Upon measurement, the X-ray powder diffractogram of each of the obtained samples is consistent with that of Form I of compound of Formula A obtained in Example 1.

TABLE 2

| Amount of compound of Formula A/solvent | Solvent | Heating temperature | Stirring time |
|---|---|---|---|
| 100 mg/3.2 mL | ethyl acetate/acetone (volume ratio 7/3) | 50-60° C. | 17 hours |
| 100 mg/3.7 mL | ethyl acetate/acetone (volume ratio 1/1) | 50-60° C. | 17 hours |
| 100 mg/4 mL | ethyl acetate/acetone (volume ratio 3/7) | 50-60° C. | 17 hours |
| 100 mg/3.4 mL | ethyl acetate/i-propanol (volume ratio 3/7) | 70-80° C. | 17 hours |
| 100 mg/2.3 mL | ethyl acetate/i-propanol (volume ratio 1/1) | 70-80° C. | 17 hours |
| 100 mg/2.4 mL | ethyl acetate/i-propanol (volume ratio 7/3) | 70-80° C. | 17 hours |

TABLE 2-continued

| Amount of compound of Formula A/solvent | Solvent | Heating temperature | Stirring time |
|---|---|---|---|
| 110 mg/2 mL | butanone | 70-80° C. | 17 hours |
| 90 mg/2 mL | butanone/ethanol (volume ratio 1/1) | 70-80° C. | 17 hours |
| 80 mg/2.2 mL | butanone/ethanol (volume ratio 1/4) | 75-85° C. | 18 hours |

Example 4 Preparation of Form I of Compound of Formula A 0.55 g of compound of Formula A was suspended in 15.5 mL of ethyl acetate, and heated to 70-80° C. to dissolve. Then the solution was cooled to 5-10° C. and stirred for 1 hour at a moderate rate. Then the precipitate was filtered and dried at 55° C. under vacuum for 16 hours to give 0.36 g of sample. Upon measurement, the X-ray powder diffractogram of the obtained sample is consistent with that of Form I of compound of Formula A obtained in Example 1.

Example 5 Preparation of Form I of Compound of Formula A 2.4 g of compound of Formula A was suspended in 265 mL of toluene, and heated to 100-110° C. to dissolve. Then the solution was cooled to 20-25° C. Then the precipitate was filtered and dried at 55° C. under vacuum for 16 hours to give 2.19 g of sample. Upon measurement, the X-ray powder diffractogram of the obtained sample is consistent with that of Form I of compound of Formula A obtained in Example 1.

Example 6 Preparation of Form I of Compound of Formula A 130 mg of compound of Formula A was suspended in 20 mL of dichloromethane, and heated to gentle reflux to dissolve. The solution was stirred under refluxing for 1 hour, and then cooled to 20-25° C. A small amount of solid precipitated. 5 mL of dichloromethane was added, and stirring continued for 4 hours. The solid sample was obtained by filtration. Upon measurement, the X-ray powder diffractogram of the obtained sample is consistent with that of Form I of compound of Formula A obtained in Example 1.

Example 7 Preparation of Form I of Compound of Formula A 100 mg of compound of Formula A was suspended in 2 mL of a mixed solvent (tetrahydrofuran/water, volume ratio 4/1), and heated to 60-70° C. to dissolve. The solution was cooled to 25-30° C., and no solid precipitated after 1 hour. Then 2 mL of water was added, and stirred for 18 hours. Then the precipitate was filtered to give the sample. Upon measurement, the X-ray powder diffractogram of the obtained sample is consistent with that of Form I of compound of Formula A obtained in Example 1.

Example 8 Preparation of Form I of Compound of Formula A 1.08 g of compound of Formula A was suspended in 37 mL of ethyl acetate, and heated to 70-80° C. to dissolve.

Then the solution was cooled to 25-30° C. and stirred for 2 hours. Then the precipitate was filtered and dried at 58° C. under vacuum for 2 hours to give the first batch of sample. Then 100 mL of isopropyl ether was added to the filtrate, and stirred for 17 hours. Then the precipitate was filtered again, and dried at 58° C. under vacuum for 2 hours to give the second batch of sample. Upon measurement, the X-ray powder diffractograms of the obtained two batches of samples are both consistent with that of Form I of compound of Formula A obtained in Example 1.

Example 9 Preparation of Form I of Compound of Formula A 120 mg of compound of Formula A was suspended in 4.5 mL of ethanol, heated to 75-85° C. to dissolve, and filtered while hot. Then 6 mL of n-heptane was added to the filtrate. The solution was cooled to 25-30° C. and stirred for 16 hours. Then the precipitate was filtered to give the sample. Upon measurement, the X-ray powder diffractogram of the obtained sample is consistent with that of Form I of compound of Formula A obtained in Example 1.

Example 10 Preparation of Form I of Compound of Formula A 110 mg of compound of Formula A was suspended in 1.2 mL of 1,4-dioxane and heated to 80-85° C. to dissolve. 1 mL of n-heptane was added. Then the solution was cooled to 20-25° C. and stirred for 18 hours. Then the precipitate was filtered and dried at 55° C. under vacuum for 4 hours to give the sample. Upon measurement, the X-ray powder diffractogram of the obtained sample is consistent with that of Form I of compound of Formula A obtained in Example 1.

Example 11 Preparation of Form I of Compound of Formula A 0.52 g of compound of Formula A was suspended in 27 mL of ethyl acetate, heated to 75-85° C. to dissolve, and filtered while hot to remove the small amount of insoluble materials. Then the filtrate was reheated to 75-85° C. to dissolve all the solids, and 5 mL of n-heptane was added. Then the mixture was cooled to 20-25° C. and stirred for 17 hours. Then the precipitate was filtered and dried at 55° C. under vacuum for 2 hours to give the sample. Upon measurement, the X-ray powder diffractogram of the obtained sample is consistent with that of Form I of compound of Formula A obtained in Example 1.

Example 12 Preparation of Form I of Compound of Formula A

The solids of compound of Formula A (a mixture of Form IV and Form V) were suspended in ethyl acetate and toluene respectively, and heated to reflux. Then the solids of compound of Formula A (a mixture of Form IV and Form V) were added till excess solids were present in each system. The obtained suspensions were stirred under reflux for 2 hours, cooled to 20-25° C., and allowed to stand for 18 hours. Then the solids were filtered respectively to give each sample. Upon measurement, the X-ray powder diffractogram of each of the obtained samples is consistent with that of Form I of compound of Formula A obtained in Example 1.

Example 13 Preparation of Form I of Compound of Formula A

The solid of compound of Formula A (a mixture of Form IV and Form V) was suspended in 0.7 mL of tetrahydrofuran, and heated to reflux. Then the solids of compound of Formula A (a mixture of Form IV and Form V) were added till excess solids were present in the system. The obtained suspension was stirred under reflux for 2 hours, and allowed to stand for 10 minutes. Then 0.5 mL of the supernatant was removed to another vial, and tetrahydrofuran in the vial was removed by purging nitrogen, followed by drying at 60° C. under vacuum for 1 hour to give the solid sample. Upon measurement, the X-ray powder diffractogram of the obtained sample is consistent with that of Form I of compound of Formula A obtained in Example 1.

Example 14 Preparation of Form I of Compound of Formula A

An appropriate amount of the solids of compound of Formula A (the forms were as listed in Table 3) were suspended in an appropriate amount of the solvents listed in Table 3 respectively. The suspensions were stirred at 25-30° C. for a period of time, and filtered respectively to give each solid sample. Upon measurement, the X-ray powder diffractogram of each of the obtained samples is consistent with that of Form I of compound of Formula A obtained in Example 1.

TABLE 3

| Amount of the solid of compound of Formula A/solvent | Form of compound of Formula A | Solvent | Stirring time |
|---|---|---|---|
| 40 mg/1 mL | Form IV | ethanol | 8 days |
| 160 mg/2.5 mL | Form V | ethyl acetate | 20 days |
| 160 mg/2.5 mL | Form V | toluene | 20 days |

Example 15 Preparation of Form IV of Compound of Formula A 3.59 g of compound of Formula A was dissolved with 100 mL of 90% ethanol by heating to 70-80° C. Then the solution was cooled to room temperature slowly and stirred at a moderate rate. Then the precipitate was collected by filtration and dried to give 1.64 g of solid.

The obtained solid sample is Form IV of compound of Formula A, the X-ray powder diffractogram of which is shown in FIG. 4. Peaks (2θ) chosen from the figure have the following values: 4.6, 7.2, 8.2, 9.2, 9.7, 11.3, 11.5, 12.0, 13.2, 13.8, 14.4, 14.7, 15.5, 16.0, 16.5, 17.8, 18.2, 19.0, 19.5, 21.1, 21.6, 22.3, 22.6, and 23.6 degrees, the measured 2θ values each having an error of about ±0.2 degrees (2θ), wherein characteristic peaks (2θ) are at 4.6, 9.2, 15.5, 17.8, and 19.0 degrees. DSC result is given in FIG. 5, showing that the endothermic peak of Form IV is at about 261.8-263.8° C.

Example 16 Preparation of Form IV of Compound of Formula A 81.2 mg of compound of Formula A was dissolved in 3 mL of ethanol under heating to reflux, and stirred for 20 minutes. After heating was stopped, the solution was cooled naturally to 20-25° C. and stirred for 1 hour at a moderate rate. Then the precipitate was filtered to give the sample. Upon measurement, the X-ray powder diffractogram of the obtained sample is consistent with that of Form IV of compound of Formula A obtained in Example 15.

Example 17 Preparation of Form IV of Compound of Formula A 81.4 mg of compound of Formula A was dissolved in 2.2 mL of 95% ethanol under heating to reflux, and stirred for 30 minutes. After heating was stopped, the solution was cooled naturally to 20-25° C. and stirred for 1 hour at a moderate rate. Then the precipitate was filtered to give the sample. Upon measurement, the X-ray powder diffractogram of the obtained sample is consistent with that of Form IV of compound of Formula A obtained in Example 15.

Example 18 Preparation of Form IV of Compound of Formula A

An appropriate amount of compound of Formula A were dissolved in various solvents under heating conditions respectively. Then each obtained solution was cooled to a certain temperature and stirred for a period of time at a moderate rate respectively. Then the precipitates were filtered respectively to give each sample (the specific conditions were as listed in Table 4). Upon measurement, the X-ray powder diffractogram of each of the obtained samples is consistent with that of Form IV of compound of Formula A obtained in Example 15.

TABLE 4

| Amount of compound of Formula A/solvent | Solvent | Heating condition | Cooling condition, temperature and stirring time |
|---|---|---|---|
| 80 mg/3.5 mL | ethanol | reflux | Cooled naturally to 20-25° C., stirred for 17 hours |
| 71.6 mg/6 mL | i-propanol | reflux | Cooled to 20-25° C. within 2-3 hours, stirred for 1 hour |
| 80 mg/3.66 mL | i-propanol/acetic acid (volume ratio 175/8) | 75-85° C. | Cooled naturally to 20-25° C., stirred for 18 hours |

TABLE 4-continued

| Amount of compound of Formula A/solvent | Solvent | Heating condition | Cooling condition, temperature and stirring time |
|---|---|---|---|
| 80 mg/1.12 mL | methanol/acetic acid (volume ratio 25/3) | 60-70° C. | Cooled naturally to 20-25° C., stirred for 18 hours |

Example 19 Preparation of Form IV of Compound of Formula A

An appropriate amount of compound of Formula A were dissolved in various solvents under heating conditions respectively. Then each obtained solution was cooled to a certain temperature and stirred for a period of time at a moderate rate respectively. Then the precipitates were filtered and dried respectively to give each sample (the specific conditions were as listed in Table 5). Upon measurement, the X-ray powder diffractogram of each of the obtained samples is consistent with that of Form IV of compound of Formula A obtained in Example 15.

TABLE 5

| Amount of compound of Formula A/solvent | Solvent | Heating condition | Cooling condition, temperature and stirring time | Drying condition |
|---|---|---|---|---|
| 10.26 g/120 mL | 80% ethanol | reflux | Cooled to 0-5° C. at 0.2° C. min$^{-1}$, stirred for 12 hours | Dried at 55° C. under vacuum for 5 hours |
| 100 mg/4.5 mL | methanol | reflux | Cooled naturally to 20-25° C., stirred for 4 hours | Dried at 55° C. under vacuum for 2 hours |
| 1.01 g/21 mL | 95% i-propanol | 80-85° C. | Cooled to 20-25° C., stirred for 18 hours; further cooled to 0-5° C., stirred for 6 hours | Dried at 55° C. under vacuum for 17 hours |
| 0.4 g/6.2 mL | 90% i-propanol | 75-85° C. | Cooled to 0-5° C., stirred for 2 hours | Dried at 55° C. under vacuum for 17 hours |
| 0.5 g/6.2 mL | 80% i-propanol | 75-85° C. | Cooled to 0-5° C., stirred for 2 hours | Dried at 55° C. under vacuum for 17 hours |
| 1.02 g/11.5 mL | 70% i-propanol | 80-85° C. | Cooled to 20-25° C., stirred for 18 hours; further cooled to 0-5° C., stirred for 6 hours | Dried at 55° C. under vacuum for 17 hours |
| 0.71 g/6 mL | 90% n-butanol | 90-100° C. | Cooled to 0-5° C., stirred for 2 hours | Dried at 55° C. under vacuum for 17 hours |

Example 20 Preparation of Form IV of Compound of Formula A 100 mg of compound of Formula A was dissolved in a mixed solvent of methanol/water (8.0 mL/1.5 mL) at 60-65° C., and kept at 60-65° C. for 30 minutes. Then the solution was cooled to 20-25° C., and only a small amount of solid precipitated. Then 7 mL of water was added to the mixture and stirring continued for 17 hours. Then the precipitate was filtered to give the sample. Upon measurement, the X-ray powder diffractogram of the obtained sample is consistent with that of Form IV of compound of Formula A obtained in Example 15.

Example 21 Preparation of Form IV of Compound of Formula A 0.99 g of compound of Formula A was dissolved in 24 mL of 95% ethanol at 75-85° C., 40 mL of water was added, and the mixture was kept at 75-85° C. for 30 minutes. Then the mixture was cooled to 20-25° C., and another 10 mL of water was added and stirred for 1 hour. Then the mixture was further cooled to 0-5° C. and stirred for 2 hours. Then the precipitate was filtered and dried at 55° C. under vacuum for 1.5 hours to give 0.80 g of sample. Upon measurement, the X-ray powder diffractogram of the obtained sample is consistent with that of Form IV of compound of Formula A obtained in Example 15.

Example 22 Preparation of Form IV of Compound of Formula A 6.05 g of compound of Formula A was dissolved in 90 mL of 80% ethanol under heating to reflux. The solution was cooled to 70° C. at a cooling rate of 0.5° C./min, and no solid precipitated; 90 mL of water was added to the solution slowly within 80 minutes, and a large amount of solid precipitated. The mixture was stirred at 70° C. for 100 minutes; cooled to 60° C. at a cooling rate of 0.5° C./min and stirred for 2 hours; then the mixture was cooled to 50° C. at a cooling rate of 0.5° C./min and stirred for 2 hours; and then the mixture was cooled to 0° C. at a cooling rate of 0.2° C./min and stirred for 5.5 hours. Then the mixture was stirred at 0-5° C. for further 5 hours. Then the precipitate was filtered, dried at room temperature for 3 days, and further dried at 55° C. under vacuum for 2 hours to give the sample. Upon measurement, the X-ray powder diffractogram of the obtained sample is consistent with that of Form IV of compound of Formula A obtained in Example 15.

Example 23 Preparation of Form IV of Compound of Formula A 5.04 g of compound of Formula A was dissolved in 65 mL of 70% i-propanol under heating to reflux. 90 mL of water was added to the solution quickly. Then the solution was cooled to 20-25° C. at a rate of 2° C./min, and stirred for 5 hours. Then the precipitate was filtered and dried at 55° C. under vacuum for 16 hours to give 4.96 g of sample. Upon measurement, the X-ray powder diffractogram of the obtained sample is consistent with that of Form IV of compound of Formula A obtained in Example 15.

Example 24 Preparation of Form IV of Compound of Formula A 190 mg of compound of Formula A was dissolved in 3.3 mL of a mixed solvent (1,4-dioxane/ethanol, volume ratio 1/5) at 80-85° C. 6 mL of water was added to the solution, cooled to 20-25° C., and stirred for 18 hours. Then the precipitate was filtered and dried at 55° C. under vacuum for 4 hours to give the sample. Upon measurement, the X-ray powder diffractogram of the obtained sample is consistent with that of Form IV of compound of Formula A obtained in Example 15.

Example 25 Preparation of Form IV of Compound of Formula A 4 g of compound of Formula A were dissolved in 60 mL of mixed solvents (tetrahydrofuran/ethanol/water, volume ratios were 1/99/25, 5/95/25, and 10/90/25 respectively) at 80-85° C. respectively, and stirred at 80-85° C. for 30 minutes. Then the solutions were cooled to 60° C. at a rate of 0.5° C./min respectively, and stirred at 60° C. for 1.5 hours. 60 mL of water were added dropwise (adding time was 1 hour) to the solutions respectively. The mixture was stirred at 60° C. for 1 hour after the addition of water; cooled to 25° C. at a rate of 0.5° C./min respectively, and stirred for 17.5 hours; cooled to 0° C. at a rate of 0.5° C./min respectively, and stirred for 2 hours. Then the solids were filtered respectively, washed with 5 mL of 40% ethanol, and dried at 55° C. under vacuum for 18 hours to give each sample. Upon measurement, the X-ray powder diffractogram of each of the obtained samples is consistent with that of Form IV of compound of Formula A obtained in Example 15.

Example 26 Preparation of Form IV of Compound of Formula A 120 mg of solid of compound of Formula A (Form I) was slurried with 4 mL of water at 75-85° C. for 1 hour. Then the suspension was cooled to 20-25° C. and stirred for 3 hours. 0.8 mL of ethanol was added to the mixture and stirring continued for 16 hours. Then the solid was filtered to give the product. Upon measurement, the X-ray powder diffractogram of the obtained sample is consistent with that of Form IV of compound of Formula A obtained in Example 15.

Example 27 Preparation of Form IV of Compound of Formula A

An appropriate amount of the solvents listed in Table 6 were placed in flasks at 20-25° C. respectively, and the solids of compound of Formula A (a mixture of Form IV and Form V) were added till excess solids were present in the solutions. Then the mixtures were heated to the temperatures listed in Table 6 respectively, and the solids of compound of Formula A (a mixture of Form IV and Form V) were added till excess solids were present in each system. Then the mixtures were stirred under the temperatures listed in Table 6 for 2 hours, cooled to 20-25° C., and allowed to stand for 18 hours respectively. Then the solids were filtered respectively to give each sample. Upon measurement, the X-ray powder diffractogram of each of the obtained samples is consistent with that of Form IV of compound of Formula A obtained in Example 15.

TABLE 6

| Solvent | Temperature |
| --- | --- |
| methanol | 60-70° C. |
| 10% methanol | 60-70° C. |
| ethanol | 70-80° C. |
| i-propanol | 75-85° C. |

Example 28 Preparation of Form IV of Compound of Formula A

An appropriate amount of the solids of compound of Formula A (the forms were as listed in Table 7) were suspended in an appropriate amount of water respectively. Then the suspensions were stirred under certain temperatures for a period of time, and filtered respectively to give each solid sample (the specific conditions were as listed in Table 7). Upon measurement, the X-ray powder diffractogram of each of the obtained samples is consistent with that of Form IV of compound of Formula A obtained in Example 15.

TABLE 7

| Amount of the solid of compound of Formula A/water | Form of compound of Formula A | Temperature | Stirring time |
|---|---|---|---|
| 40 mg/2 mL | Form VI | 20-25° C. | 4 days |
| 30 mg/1 mL | Form I | 25-30° C. | 8 days |
| 30 mg/1 mL | Form IV | 25-30° C. | 8 days |
| 30 mg/1 mL | Form V | 25-30° C. | 8 days |
| 200 mg/5 mL | Form VIII | 20-25° C. | 1 day |

Example 29 Preparation of Form IV of Compound of Formula A

An appropriate amount of the solid of compound of Formula A (Form VI) was heated at 120° C. under vacuum for 3 hours to give the sample. Alternatively, an appropriate amount of the solid of compound of Formula A (Form VI) was dried under vacuum firstly at 50° C. for 0.5 hour, then at 55° C. for 4 hours, and finally at 120° C. for 0.5 hour to give the sample. Upon measurement, the X-ray powder diffractogram of each of the obtained samples is consistent with that of Form IV of compound of Formula A obtained in Example 15.

Example 30 Preparation of Form V of Compound of Formula A 0.83 g of compound of Formula A was suspended in 85 mL of acetonitrile, and heated to 70-80° C. to dissolve. Then the solution was cooled to 20-25° C. and stirred for 17 hours at a moderate rate. Then the precipitate was filtered and dried at 60° C. under vacuum for 1 hour to give 0.62 g of solid. The obtained powder sample is Form V of compound of Formula A, the X-ray powder diffractogram of which is shown in FIG. 7. Peaks (2θ) chosen from the figure have the following values: 4.6, 7.3, 8.9, 10.0, 11.2, 11.6, 13.5, 14.6, 15.5, 16.0, 17.7, 18.0, 19.3, 20.0, 22.7, 23.4, 24.0, 25.1, 26.0, 27.2, 28.4, and 29.7 degrees, the measured 2θ values each having an error of about ±0.2 degrees (2θ), wherein characteristic peaks (2θ) are at 7.3, 11.6, 14.6, 19.3, and 23.4 degrees. DSC result is given in FIG. 8, showing that the endothermic peak of Form V is at about 261.4-262.4° C.

Example 31 Preparation of Form V of Compound of Formula A 700 mg of compound of Formula A was suspended in a mixed solvent of acetonitrile/acetic acid (20 mL/1.4 mL), and heated to 75-80° C. to dissolve. Then the solution was cooled to 20-25° C. and stirred for 1 hour at a moderate rate. Then the precipitate was filtered and dried at 55° C. under vacuum for 1 hour to give 300 mg of solid. Upon measurement, the X-ray powder diffractogram of the obtained sample is consistent with that of Form V of compound of Formula A obtained in Example 30.

Example 32 Preparation of Form V of Compound of Formula A 1 g of compound of Formula A was suspended in 50 mL of 90% acetonitrile, and heated to 70-80° C. to dissolve. Then the solution was cooled to 20-25° C. and stirred for 15 hours at a moderate rate; then further cooled to −10--5° C. and stirred for 3 hours at a moderate rate. Then the precipitate was filtered and dried at 60° C. under vacuum for 16 hours to give 0.72 g of solid. Upon measurement, the X-ray powder diffractogram of the obtained sample is consistent with that of Form V of compound of Formula A obtained in Example 30.

Example 33 Preparation of Form V of Compound of Formula A

An appropriate amount of compound of Formula A were suspended in an appropriate amount of the solvents listed in Table 8 respectively. The suspensions were heated to the temperatures listed in Table 8 to dissolve. Then the solutions were cooled to 20-25° C. and stirred for a period of time at a moderate rate. Then the precipitates were filtered respectively to give each sample. Upon measurement, the X-ray powder diffractogram of each of the obtained samples is consistent with that of Form V of compound of Formula A obtained in Example 30.

TABLE 8

| Amount of compound of Formula A/solvent | Solvent | Heating temperature | Stirring time |
|---|---|---|---|
| 80 mg/2.36 mL | acetonitrile/acetic acid (volume ratio 55/4) | 75-80° C. | 18 hours |
| 80 mg/3.2 mL | acetone/ethanol (volume ratio 1/4) | 55-60° C. | 17 hours |
| 90 mg/6 mL | ethyl acetate/acetonitrile (volume ratio 3/7) | 70-80° C. | 17 hours |
| 110 mg/6 mL | butanone/acetonitrile (volume ratio 1/1) | 70-80° C. | 17 hours |
| 90 mg/3.8 mL | tetrahydrofuran/acetonitrile (volume ratio 3/7) | 60-70° C. | 17 hours |

Example 34 Preparation of Form V of Compound of Formula A

The solid of compound of Formula A (a mixture of Form IV and Form V) was suspended in an appropriate amount of acetonitrile, and heated to reflux. Then the solids of compound of Formula A (a mixture of Form IV and Form V) were added till excess solids were present in the system. The obtained suspension was stirred under reflux for 2 hours, cooled to 20-25° C., and allowed to stand for 18 hours. Then the solid was filtered to give the sample. Upon measurement, the X-ray powder diffractogram of the obtained sample is consistent with that of Form V of compound of Formula A obtained in Example 30.

Example 35 Preparation of Form V of Compound of Formula A 160 mg of sample of Form I of compound of Formula A and 180 mg of sample of Form IV of compound of Formula A were mixed with 8 mL of acetonitrile respectively, stirred at 70-80° C. for 4 hours, and then cooled to 22-28° C. and stirred for 7 days. Another 3 mL of acetonitrile was added to each mixture respectively. The mixtures were reheated to 70-80° C. and stirred for 4 hours; then cooled to 22-28° C. and stirred for 16 hours. Then the solids were filtered respectively and dried at 50° C. under vacuum for 30 minutes to give each sample. Upon measurement, the X-ray powder diffractogram of each of the obtained samples is consistent with that of Form V of compound of Formula A obtained in Example 30.

Example 36 Preparation of Form VI of Compound of Formula A 3 g of compound of Formula A was suspended in 130 mL of acetone, and heated to 55-60° C. to dissolve. Then the solution was cooled to 25-30° C. and stirring continued for about 18 hours. Then the precipitate was filtered and dried in the air for 30 minutes to give 2.15 g of product. The content of acetone (gas chromatography, GC): 10.86%.

The obtained powder sample is Form VI of compound of Formula A, the X-ray powder diffractogram of which is shown in FIG. 10. Peaks (2θ) chosen from the figure have the following values: 6.9, 8.6, 9.0, 9.8, 10.4, 12.0, 13.4, 15.0, 15.8, 16.2, 16.8, 17.3, 18.0, 18.2, 18.9, 19.4, 19.7, 20.6, 21.0, 21.6, 22.5, 23.0, 23.3, 23.8, 24.5, 25.0, 26.2, and 29.8 degrees, the measured 2θ values each having an error of about ±0.2 degrees (2θ), wherein characteristic peaks (2θ) are at 8.6, 10.4, 12.0, 15.0, and 19.7 degrees. DSC result is given in FIG. 11, showing that the endothermic peaks of Form VI are at about 97.3-106.0° C. and about 262.3-265.0° C.

Example 37 Preparation of Form VI of Compound of Formula A

Compound of Formula A was dissolved in 2.5 mL of 95% acetone to saturation at 40-45° C., and filtered while hot to remove the insoluble materials. Then the filtrate was cooled to 20-25° C. and stirring continued for 2 hours. Then the precipitate was filtered to give the product. Upon measurement, the X-ray powder diffractogram of the obtained sample is consistent with that of Form VI of compound of Formula A obtained in Example 36.

Example 38 Preparation of Form VI of Compound of Formula A 80 mg of compound of Formula A was suspended in 3.7 mL of acetone, heated to 50-60° C. to dissolve, and stirred for 30 minutes. Then the mixture was filtered. Then the solution was cooled to 0-5° C. quickly with ice-bath and was stirred for further 1 hour. Then the precipitate was filtered to give the sample. Upon measurement, the X-ray powder diffractogram of the obtained sample is consistent with that of Form VI of compound of Formula A obtained in Example 36.

Example 39 Preparation of Form VI of Compound of Formula A 80 mg of compound of Formula A was suspended in 8 mL of a mixed solvent of acetone/i-propanol (volume ratio 7/3), and heated to 50-60° C. to dissolve. Then heating was stopped, and the solution was cooled naturally to 20-25° C. Then the precipitate was filtered to give the sample. Upon measurement, the X-ray powder diffractogram of the obtained sample is consistent with that of Form VI of compound of Formula A obtained in Example 36.

Example 40 Preparation of Form VI of Compound of Formula A 700 mg of compound of Formula A was suspended in 20 mL of a mixed solvent of acetone/water (volume ratio 3/1), heated to 50-60° C. to dissolve, and filtered while hot. Then the filtrate was cooled to 20-25° C. and was stirred for further 1 hour; further cooled to 0-5° C. and stirred for 30 minutes. Then a small amount of sample was filtered to give the first batch of sample. Then 30 mL of water was added to the rest mixture and stirring continued at 20-25° C. for 17 hours. Then the precipitate was filtered to give the second batch of sample. Upon measurement, the X-ray powder diffractograms of the obtained two batches of samples are consistent with that of Form VI of compound of Formula A obtained in Example 36.

Example 41 Preparation of Form VI of Compound of Formula A 70 mg of the solid of compound of Formula A (a mixture of Form I and Form V) was suspended in 0.9 mL of a mixed solvent of acetone/water (volume ratio 3/1), stirred at 25-30° C. for 6 days, and filtered to give the solid. Upon measurement, the X-ray powder diffractogram of the obtained sample is consistent with that of Form VI of compound of Formula A obtained in Example 36.

Example 42 Preparation of Form VIII of Compound of Formula A 10.2 g of compound of Formula A was mixed with 130 mL of 70% i-propanol, heated to reflux to dissolve, and stirred at 75-80° C. for 30 minutes. Then the solution was cooled to 45-55° C. and stirred for further 2 hours; further cooled to 23-30° C. and stirred for about 6 days. Then the precipitate was filtered and dried in the air for 100 minutes to give the product. The content of water (KF): 10.8%; the content of i-propanol (gas chromatography, GC): 6.8%.

The obtained powder sample is Form VIII of compound of Formula A, the X-ray powder diffractogram of which is shown in FIG. 13. Peaks (2θ) chosen from the figure have the following values: 7.0, 8.3, 9.8, 10.7, 11.4, 13.3, 13.8, 14.2, 15.3, 15.7, 17.7, 19.0, 19.4, 19.6, 20.3, 21.4, 22.4, 23.1, 23.5, 24.0, 25.0, 25.4, 26.9, and 27.2 degrees, the measured 2θ values each having an error of about ±0.2 degrees (2θ), wherein characteristic peaks (2θ) are at 7.0, 8.3, 11.4, 15.3, and 23.1 degrees. DSC result is given in FIG. 14, showing that the endothermic peaks of Form VIII are at about 64.1-81.7° C. and about 261.5-262.2° C.

Example 43 Preparation of Form VIII of Compound of Formula A 3.9 g of the sample of Form IV of compound of Formula A was suspended in 50 mL of 70% i-propanol, and stirred at room temperature for 3 days to give the first batch of sample for testing. The suspension was stirred for further 3 days. 10 mL of 70% i-propanol was added to the suspension and stirring continued for 2 days. Then the solid was collected by filtration, and dried at room temperature in the air for 50 minutes to give the second batch of sample. Upon measurement, the X-ray powder diffractograms of the obtained two batches of samples are consistent with that of Form VIII of compound of Formula A obtained in Example 42.

Example 44 Preparation of Form VIII of Compound of Formula A 200 mg of the sample of Form IV of compound of Formula A was suspended in 4 mL of 90% i-propanol. The mixture was stirred at 20-25° C. for 4 days, and filtered to give the solid. Upon measurement, the X-ray powder diffractogram of the obtained sample is consistent with that of Form VIII of compound of Formula A obtained in Example 42.

Example 45 Stability of Form I, Form IV, and Form V Under High Temperature, High Humidity and Illumination Conditions Determination method: the test samples of Form I, Form IV, and Form V of compound of Formula A were placed on the culture dishes respectively, which were uncovered and placed in sealed clean containers. The containers were placed under the conditions of a temperature of 60° C., a temperature of 25° C. and a relative humidity of 92.5%±5%, and an illumination of 4500lx±500lx respectively for 10 days. Then sampled, investigated for the purity and crystalline form of the samples, and compared the investigation results. The results were shown in Table 9.

TABLE 9

| Test condition | High temperature (60° C.) | | High humidity (92.5% RH) | | Illumination (4500 Lx) | |
|---|---|---|---|---|---|---|
| Sampling time | 0 0 day | 5 days | 10 days | 5 days | 10 days | 5 days | 10 days |
| Form Chemical purity (%) | I 99.76 | I 99.63 | I 99.63 | I 99.65 | I 99.60 | I 99.61 | I 99.45 |
| Form Chemical purity (%) | IV 99.27 | IV 99.57 | IV 99.68 | IV 99.68 | IV 99.68 | IV 99.59 | IV 99.55 |
| Form Chemical purity (%) | V 99.70 | V 99.88 | V 99.87 | V 99.88 | V 99.87 | V 99.85 | V 99.81 |

Conclusion: the data in Table 9 illustrate that, the chemical purity and crystalline form of Form I, Form IV, and Form V of compound of Formula A are not changed after placed under high temperature, high humidity, and illumination conditions for 10 days, showing that Form I, Form IV, and Form V are stable.

Example 46 Stability of Form IV Mixed with Excipients

Determination method: 50 mg of samples of Form IV of compound of Formula A were mixed with 200 mg of excipients starch and microcrystalline cellulose respectively. The mixtures were used as test samples and placed on the culture dishes respectively, which were uncovered and placed in sealed clean containers. Then the containers were placed under the conditions of a temperature of 60° C., a temperature of 25° C. and a relative humidity of 92.5%±5%, and an illumination of 4500lx±500lx respectively for 30 days. Then sampled, investigated for the change of crystalline form of the samples, and compared the investigation results. The results were shown in Table 10.

TABLE 10

| Test material | Test time | Test condition | Test result |
|---|---|---|---|
| Mixture of starch | | Form 0 day | Form IV Form IV |
| | 30 days | High temperature (60° C.) | Form IV |
| | | High humidity (92.5% RH) | Form IV |
| | | illumination (4500 Lx) | Form IV |

TABLE 10-continued

| Test material | Test time | Test condition | Test result |
|---|---|---|---|
| Mixture of microcrystalline cellulose | 30 days | 0 day | Form IV |
| | | High temperature (60° C.) | Form IV |
| | | High humidity (92.5% RH) | Form IV |
| | | illumination (4500 Lx) | Form IV |

Conclusion: the data in Table 10 illustrate that, the mixtures of Form IV of compound of Formula A with starch or microcrystalline cellulose are stable under high temperature, high humidity, and illumination conditions, indicating that Form IV is stable under the test conditions.

Example 47 Solubility of Form I, Form IV, and Form V in Different Buffers

Determination method: excess amount of samples of Form I, Form IV, and Form V of compound of Formula A were suspended in the buffers of different pH respectively. The system was saturated by shaking for a period of time at 37° C. in a water bath of constant temperature. Then the system was filtered, and the filtrate was used for determining solubility of the samples. The solubility of each Form was shown in Table 11. The buffers of different pH were prepared according to the US pharmacopeia (USP40-NF35).

TABLE 11

| pH value of buffer | Solubility (mg/mL) | | |
|---|---|---|---|
| | Form I* | Form IV** | Form V** |
| pH 1.2 | 10.78 | 8.56 | 9.64 |
| pH 2.1 | 0.8 | 0.5 | 0.58 |
| pH 4.5 | 0.04 | 0.02 | 0.02 |
| pH 6.8 | 0.03 | 0.02 | 0.02 |

*shaken at 37° C. water bath for 0.5 hour,
**shaken at 37° C. water bath for 2 hours.

Conclusion: the data in Table 11 illustrate that, in the test buffers, Form I, Form IV, and Form V of compound of Formula A all have good solubility.

Example 48 Hygroscopicity of Form I, Form IV, and Form V

Determination method: the test samples of Form I, Form IV, and Form V of compound of Formula A were placed in the sample dishes of the dynamic vapor sorption instrument (DVS-INTRINSIC) respectively. Then the weight gains by moisture absorption of the samples were measured at a relative humidity of 0-95% at 25° C. The results were shown in FIG. 16, FIG. 17, and FIG. 18.

Figure 16:
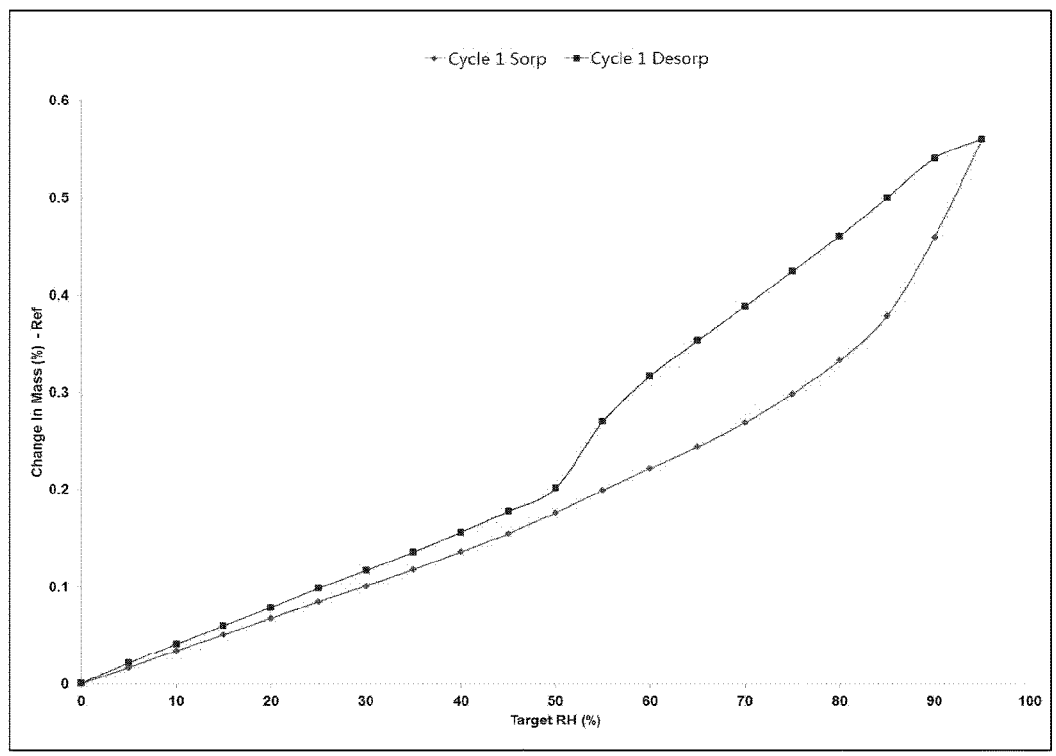
FIG. 16 shows a dynamic vapor sorption (DVS) isotherm Plot of Form I of compound of Formula A, wherein the horizontal axis (X-axis) plots the relative humidity (%), and the vertical axis (Y-axis) plots the weight change percentage (%).
Figure 17:
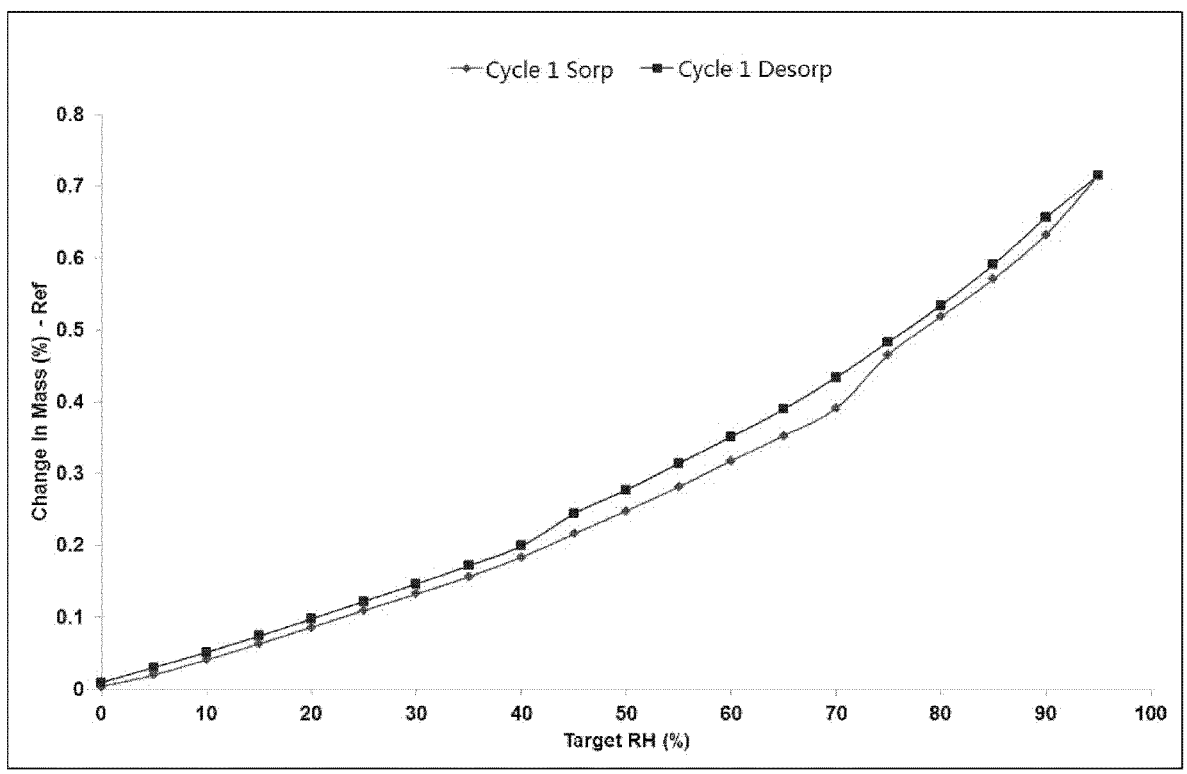
FIG. 17 shows a dynamic vapor sorption (DVS) isotherm Plot of Form IV of compound of Formula A, wherein the horizontal axis (X-axis) plots the relative humidity (%), and the vertical axis (Y-axis) plots the weight change percentage (%).
Figure 18:
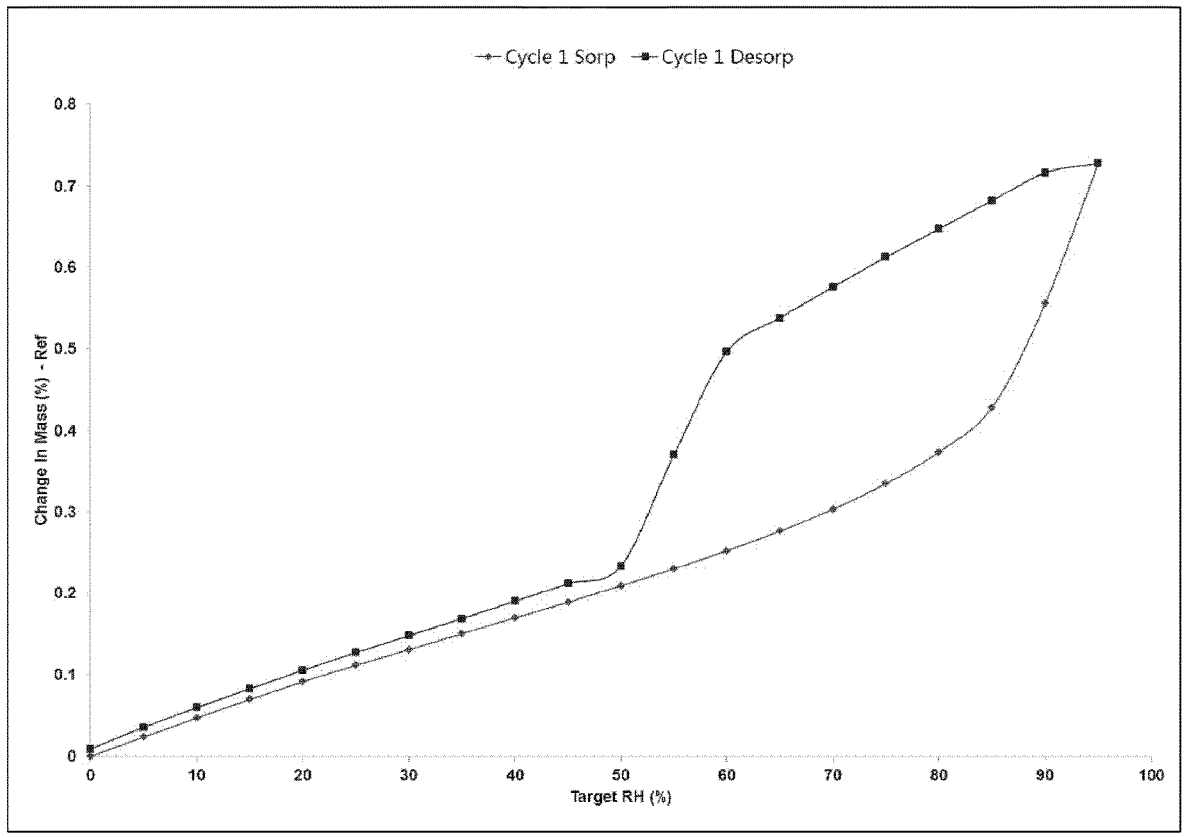
FIG. 18 shows a dynamic vapor sorption (DVS) isotherm Plot of Form V of compound of Formula A, wherein the horizontal axis (X-axis) plots the relative humidity (%), and the vertical axis (Y-axis) plots the weight change percentage (%).

Conclusion: the curves in FIG. 16, FIG. 17, and FIG. 18 illustrate that, Form I, Form IV, and Form V of compound of Formula A all are non-hygroscopic.

It is to be understood that, the examples and embodiments described herein are only for interpretation purposes, and various improvements or modifications in view of these would be suggested to those skilled in the art and are within the spirit and scope of present application and the scope of the appended claims. All the publications, patents and patent applications cited herein are incorporated herein by reference for all purposes.

What is claimed:

1. A crystalline form of (S)-4-amino-6-((1-(3-chloro-6-phenylimidazo[1,2-b]pyridazin-7-yl)ethyl)amino)pyrimidine-5-carbonitrile of the Formula A:

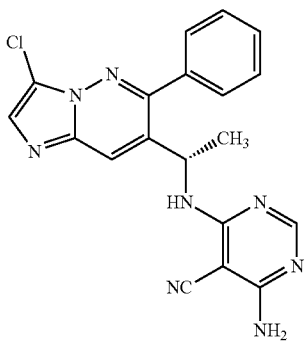

Formula A wherein the crystalline form is Form IV; and
wherein crystalline Form IV is characterized by an X-ray powder diffractogram comprising characteristic peaks at diffraction angles (°2θ) of 4.6°±0.2 °2θ, 9.2°±0.2 °2θ, 15.5°±0.2 °2θ, 17.8°±0.2 °2θ, and 19.0°±0.2 °2θ.

2. The crystalline form of claim 1, wherein the crystalline form is further characterized by an X-ray powder diffractogram comprising additional characteristic peaks at diffraction angles (°2θ) of 11.5°±0.2 °2θ, 12.0°±0.2 °2θ, 13.2°±0.2 °2θ, 16.0°±0.2 °2θ, and 22.6°±0.2 °2θ.

3. The crystalline form of claim 1, wherein the crystalline form has less than 40% by weight of other crystalline forms of (S)-4-amino-6-((1-(3-chloro-6-phenylimidazo[1,2-b]pyridazine-7-yl)ethyl)amino)pyrimidine-5-carbonitrile.

4. The crystalline form of claim 3, wherein the crystalline form has less than 30% by weight of other crystalline forms of (S)-4-amino-6-((1-(3-chloro-6-phenylimidazo[1,2-b]pyridazine-7-yl)ethyl)amino)pyrimidine-5-carbonitrile.

5. The crystalline form of claim 3, wherein the crystalline form has less than 20% by weight of other crystalline forms of (S)-4-amino-6-((1-(3-chloro-6-phenylimidazo[1,2-b]pyridazine-7-yl)ethyl)amino)pyrimidine-5-carbonitrile.

6. The crystalline form of claim 3, wherein the crystalline form has less than 10% by weight of other crystalline forms of (S)-4-amino-6-((1-(3-chloro-6-phenylimidazo[1,2-b]pyridazine-7-yl)ethyl)amino)pyrimidine-5-carbonitrile.

7. The crystalline form of claim 3, wherein the crystalline form has less than 5% by weight of other crystalline forms of (S)-4-amino-6-((1-(3-chloro-6-phenylimidazo[1,2-b]pyridazine yl)ethyl)amino)pyrimidine-5-carbonitrile.

8. The crystalline form of claim 3, wherein the crystalline form has less than 1% by weight of other crystalline forms of (S)-4-amino-6-((1-(3-chloro-6-phenylimidazo[1,2-b]pyridazine yl)ethyl)amino)pyrimidine-5-carbonitrile.

9. A pharmaceutical composition comprising one or more pharmaceutically acceptable carriers and an effective amount of the crystalline form of claim 1.

10. A method for inhibiting phosphatidylinositol-3 kinase activity in a subject, wherein the method comprises administering to the subject in need thereof an effective amount of the crystalline form of claim 1.

11. The method of claim 10, wherein the subject has a disease associated with phosphatidylinositol-3 kinase activity selected from the group consisting of an autoimmune disease, an inflammatory disease, and cancer.

12. The method of claim 11, wherein the cancer is a hematological malignancy.

13. The method of claim 11, wherein the autoimmune disease, inflammatory disease, or cancer is selected from the group consisting of allergic rhinitis, asthma, chronic obstructive pulmonary disease, leukemia, lymphoma, multiple myeloma, multiple sclerosis, psoriasis, rheumatoid arthritis, systemic lupus erythematosus, and Waldenstrom's macroglobulinemia.

14. The method of claim 13, wherein the leukemia is selected from the group consisting of acute lymphocytic leukemia, acute myelogenous leukemia, chronic lymphocytic leukemia, and chronic myelogenous leukemia.

15. The method of claim 13, wherein the lymphoma is selected from the group consisting of B-cell lymphoma, Burkitt lymphoma, follicular lymphoma, Hodgkin's lymphoma, mantle cell lymphoma, marginal zone lymphoma, natural killer cell lymphoma, non-Hodgkin's lymphoma, small lymphocytic lymphoma, and T-cell lymphoma.

16. The method of claim 15, wherein the B-cell lymphoma is diffuse large B-cell lymphoma.

17. A process for preparing the crystalline form of (S)-4-amino-6-((1-(3-chloro-6-phenylimidazo[1,2-b]pyridazin-7-yl)ethyl)amino)pyrimidine-5-carbonitrile of the Formula A of claim 1:

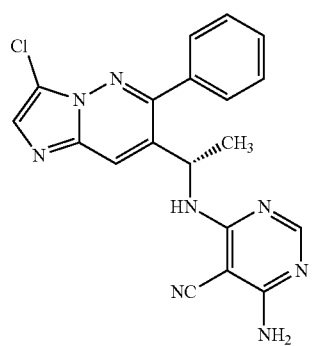

Formula A wherein the crystalline form is Form IV; and
wherein crystalline Form IV is characterized by an X-ray powder diffractogram comprising characteristic peaks at diffraction angles (°2θ) of 4.6°±0.2 °2θ, 9.2°±0.2 °2θ, 15.5°±0.2 °2θ, 17.8°±0.2 °2θ, and 19.0°±0.2 °2θ;
wherein the process comprises the following steps:
(1) mixing (S)-4-amino-6-((1-(3-chloro-6-phenylimidazo[1,2-b]pyridazin-7-yl)ethyl)amino)pyrimidine carbonitrile with:
(a) at least one dissolution solvent selected from the group consisting of (i) methanol, ethanol, isopropanol, or n-butanol, (ii) a mixture of acetic acid and isopropanol, and (iii) a mixture of acetic acid and methanol; or
(b) a mixed solvent consisting of water and a water-miscible organic solvent selected from the group consisting of methanol, ethanol, isopropanol, and n-butanol;
and heating the mixture to reflux to obtain a solution;
(2) cooling the solution obtained in step (1) above until (S)-4-amino-6-((1-(3-chloro-6-phenylimidazo[1,2b]pyridazin-7-yl)ethyl)amino)pyrimidine-5-carbonitrile precipitates;
(3) isolating Form IV of (S)-4-amino-6-((1-(3-chloro-6-phenylimidazo[1,2-b]pyridazin-7-yl)ethyl)amino)pyrimidine-5-carbonitrile of the Formula A; and (4) optionally drying Form IV of (S)-4-amino-6-((1-(3-chloro-6-phenylimidazo[1,2-b]pyridazin-7-yl)ethyl)amino)pyrimidine-5-carbonitrile of the Formula A obtained in step (3) above.

18. The process of claim 17, wherein the crystalline form is further characterized by an X-ray powder diffractogram comprising additional characteristic peaks at diffraction angles (°2θ) of 11.5°±0.2 °2θ, 12.0°±0.2 °2θ, 13.2°±0.2 °2θ, 16.0°±0.2 °2θ, and 22.6°±0.2 °2θ.

19. A process for preparing the crystalline form of (S)-4-amino-6-((1-(3-chloro-6-phenylimidazo[1,2-b]pyridazin-7-yl)ethyl)amino)pyrimidine-5-carbonitrile of the Formula A of claim 1:

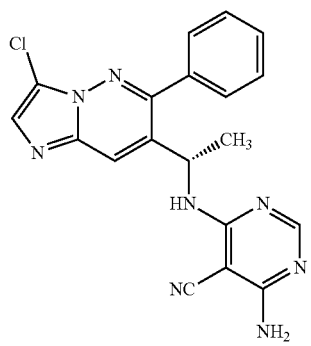

Formula A wherein the crystalline form is Form IV; and wherein crystalline Form IV is characterized by an X-ray powder diffractogram comprising characteristic peaks at diffraction angles (°2θ) of 4.6°±0.2 °2θ, 9.2°±0.2 °2θ, 15.5°±0.2 °2θ, 17.8°±0.2 °2θ, and 19.0°±0.2 °2θ;

wherein the process comprises the following steps:

(1) mixing (S)-4-amino-6-((1-(3-chloro-6-phenylimidazo[1,2-b]pyridazin-7-yl)ethyl)amino)pyrimidine carbonitrile with:

(a) at least one dissolution solvent selected from the group consisting of (i) methanol, (ii) ethanol, (iii) isopropanol, and (iv) a mixture of ethanol and 1,4-dioxane; or (b) a mixed solvent consisting of water and a water-miscible organic solvent selected from the group consisting of (i) methanol, ethanol, or isopropanol, and (ii) a mixture of ethanol and tetrahydrofuran;

and heating the mixture to reflux to obtain a first solution;

(2) adding water to the first solution obtained in step (1) above, to obtain a second solution;

(3) cooling the second solution obtained in step (2) above until (S)-4-amino-6-((1-(3-chloro-6-phenylimidazo[1,2-b]pyridazin-7-yl)ethyl)amino)pyrimidine-5-carbonitrile of the Formula A precipitates;

(4) isolating Form IV of (S)-4-amino-6-((1-(3-chloro-6-phenylimidazo[1,2-b]pyridazin-7-yl)ethyl)amino)pyrimidine-5-carbonitrile of the Formula A; and (5) optionally drying Form IV of (S)-4-amino-6-((1-(3-chloro-6-phenylimidazo[1,2-b]pyridazin-7-yl)ethyl)amino)pyrimidine-5-carbonitrile of the Formula A obtained in step (4) above.

20. A process for preparing the crystalline form of (S)-4-amino-6-((1-(3-chloro-6-phenylimidazo[1,2-b]pyridazin-7-yl)ethyl)amino)pyrimidine-5-carbonitrile of the Formula A of claim 1:

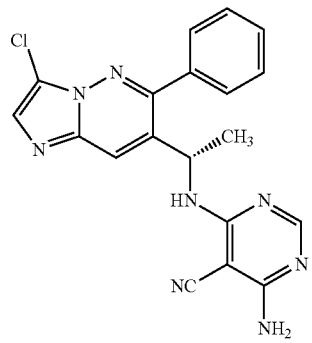

Formula A wherein the crystalline form is Form IV; and wherein crystalline Form IV is characterized by an X-ray powder diffractogram comprising characteristic peaks at diffraction angles (°2θ) of 4.6°±0.2 °2θ, 9.2°±0.2 °2θ, 15.5°±0.2 °2θ, 17.8°±0.2 °2θ, and 19.0°±0.2 °2θ;

wherein the process comprises the following steps:

(1) mixing (S)-4-amino-6-((1-(3-chloro-6-phenylimidazo[1,2-b]pyridazin-7-yl)ethyl)amino)pyrimidine carbonitrile with:

(a) at least one dissolution solvent selected from the group consisting of (i) methanol, (ii) ethanol, (iii) isopropanol, and (iv) a mixture of ethanol and 1,4-dioxane; or (b) a mixed solvent consisting of water and a water-miscible organic solvent selected from the group consisting of (i) methanol, ethanol, or isopropanol, and (ii) a mixture of ethanol and tetrahydrofuran;

and heating the mixture to reflux to obtain a first solution;

(2) cooling the first solution obtained in step (1) above, to obtain a second solution;

(3) adding water to the second solution obtained in step (2) above until (S)-4-amino-6-((1-(3-chloro-6-phenylimidazo[1,2-b]pyridazin-7-yl)ethyl)amino)pyrimidine-5-carbonitrile of the Formula A precipitates;

(4) isolating Form IV of (S)-4-amino-6-((1-(3-chloro-6-phenylimidazo[1,2-b]pyridazin-7-yl)ethyl)amino)pyrimidine-5-carbonitrile of the Formula A; and (5) optionally drying Form IV of (S)-4-amino-6-((1-(3-chloro-6-phenylimidazo[1,2-b]pyridazin-7-yl)ethyl)amino)pyrimidine-5-carbonitrile of the Formula A obtained in step (4) above.

21. A process for preparing the crystalline form of (S)-4-amino-6-((1-(3-chloro-6-phenylimidazo[1,2-b]pyridazin-7-yl)ethyl)amino)pyrimidine-5-carbonitrile of the Formula A of claim 1:

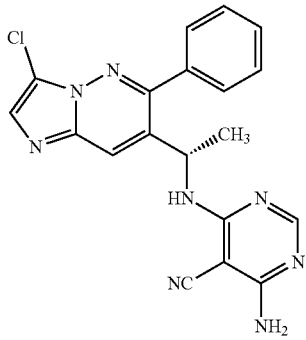

Formula A wherein the crystalline form is Form IV; and
wherein crystalline Form IV is characterized by an X-ray powder diffractogram comprising characteristic peaks at diffraction angles (2θ) of 4.6°±0.2 °2θ, 9.2°±0.2 °2θ, 15.5°±0.2 °2θ, 17.8°±0.2 °2θ, and 19.0°±0.2 °2θ;
wherein the process comprises the following steps:
(1) suspending (S)-4-amino-6-((1-(3-chloro-6-phenylimidazo[1,2-b]pyridazin yl)ethyl)amino)pyrimidine-5-carbonitrile in a solvent selected from the group consisting of (i) methanol, (ii) isopropanol, (iii) water, and (iv) a mixture of methanol and water;
(2) stirring the suspension obtained in step (1) above;
(3) isolating Form IV of (S)-4-amino-6-((1-(3-chloro-6-phenylimidazo[1,2-b]pyridazin yl)ethyl)amino)pyrimidine-5-carbonitrile of the Formula A; and
(4) optionally drying Form IV of (S)-4-amino-6-((1-(3-chloro-6-phenylimidazo[1,2-b]pyridazin-7-yl)ethyl)amino)pyrimidine-5-carbonitrile of the Formula A obtained in step (3) above.

22. A process for preparing the crystalline form of (S)-4-amino-6-((1-(3-chloro-6-phenylimidazo[1,2-b]pyridazin-7-yl)ethyl)amino)pyrimidine-5-carbonitrile of the Formula A of claim 1:

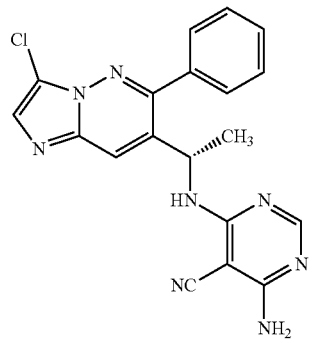

Formula A wherein the crystalline form is Form IV; and
wherein crystalline Form IV is characterized by an X-ray powder diffractogram comprising characteristic peaks at diffraction angles (°2θ) of 4.6°±0.2 °2θ, 9.2°±0.2 °2θ, 15.5°±0.2 °2θ, 17.8°±0.2 °2θ, and 19.0°±0.2 °2θ;
wherein the process comprises the following steps:
(1) suspending (S)-4-amino-6-((1-(3-chloro-6-phenylimidazo[1,2-b]pyridazin-7-yl)ethyl)amino)pyrimidine-5-carbonitrile in ethanol;
(2) stirring the suspension obtained in step (1) above for less than 24 hours;
(3) isolating Form IV of (S)-4-amino-6-((1-(3-chloro-6-phenylimidazo[1,2-b]pyridazin-7-yl)ethyl)amino)pyrimidine-5-carbonitrile of the Formula A; and
(4) optionally drying Form IV of (S)-4-amino-6-((1-(3-chloro-6-phenylimidazo[1,2-b]pyridazin yl)ethyl)amino)pyrimidine-5-carbonitrile of the Formula A obtained in step (3) above.

\* \* \* \* \*